United States Patent
Bardy et al.

(10) Patent No.: US 11,647,941 B2
(45) Date of Patent: May 16, 2023

(54) SYSTEM AND METHOD FOR FACILITATING A CARDIAC RHYTHM DISORDER DIAGNOSIS WITH THE AID OF A DIGITAL COMPUTER

(71) Applicant: Bardy Diagnostics, Inc., Bellevue, WA (US)

(72) Inventors: Gust H. Bardy, Carnation, WA (US); Ezra M. Dreisbach, Vashon, WA (US); Shawni L. Daw, Redmond, WA (US); Rodney Boleyn, Bellevue, WA (US); Brian W. Epps, Bainbridge Island, WA (US)

(73) Assignee: Bardy Diagnostics, Inc., Bellevue, WA (US)

( * ) Notice: Subject to any disclaimer, the term of this patent is extended or adjusted under 35 U.S.C. 154(b) by 0 days.

(21) Appl. No.: 17/533,006

(22) Filed: Nov. 22, 2021

(65) Prior Publication Data
US 2022/0079497 A1    Mar. 17, 2022

Related U.S. Application Data

(63) Continuation of application No. 17/067,466, filed on Oct. 9, 2020, now Pat. No. 11,179,087, which is a (Continued)

(51) Int. Cl.
*A61B 5/352* (2021.01)
*A61B 5/00* (2006.01)
(Continued)

(52) U.S. Cl.
CPC ............ *A61B 5/352* (2021.01); *A61B 5/0245* (2013.01); *A61B 5/02405* (2013.01);
(Continued)

(58) Field of Classification Search
None
See application file for complete search history.

(56) References Cited

U.S. PATENT DOCUMENTS

| | | |
|---|---|---|
| 3,215,136 A | 11/1965 | Holter et al. |
| 3,569,852 A | 3/1971 | Berkovits |

(Continued)

FOREIGN PATENT DOCUMENTS

| | | |
|---|---|---|
| DE | 19955211 | 5/2001 |
| EP | 1859833 | 11/2007 |
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |

(Continued)

OTHER PUBLICATIONS

Pranav Rajpurkar et al. "Cardiologist-Level Arrhythmia Detection with Convolutional Neural Networks,"arxiv.org, Cornell University Library, 201 Olin Library Cornell University Ithaca, NY 14853, Jul. 6, 2017 (Jul. 6, 2017), XP080774895.

(Continued)

*Primary Examiner* — Kennedy Schaetzle
(74) *Attorney, Agent, or Firm* — Patrick J. S. Inouye; Krista A. Wittman

(57) ABSTRACT

A system for facilitating a cardiac rhythm disorder diagnosis is provided. A download station is adapted to retrieve cutaneous action potentials of a patient recorded as ECG data. A plot of R-R interval data is generated based on the ECG data and displayed. A presentation of the R-R interval data in the display is changed by identifying a section of the R-R interval data and removing portions of the R-R interval data associated with an earlier recordation time than the R-R interval data in the section and a later recordation time than the R-R interval data in the section. The R-R interval data remaining in the display is provided in greater detail. Report strips are generated from the remaining R-R interval data and classified with a cardiac condition of the patient.

20 Claims, 26 Drawing Sheets

Related U.S. Application Data continuation of application No. 16/537,408, filed on Aug. 9, 2019, now Pat. No. 10,799,137, which is a continuation-in-part of application No. 16/102,608, filed on Aug. 13, 2018, now Pat. No. 10,736,532, which is a continuation of application No. 15/231,752, filed on Aug. 8, 2016, now Pat. No. 10,045,709, which is a continuation of application No. 15/066,883, filed on Mar. 10, 2016, now Pat. No. 9,408,551, which is a continuation-in-part of application No. 14/997,416, filed on Jan. 15, 2016, now Pat. No. 9,345,414, said application No. 14/997,416 is a continuation-in-part of application No. 14/614,265, filed on Feb. 4, 2015, now Pat. No. 9,408,545, which is a continuation-in-part of application No. 14/488,230, filed on Sep. 16, 2014, now Pat. No. 9,700,227, which is a continuation-in-part of application No. 14/080,725, filed on Nov. 14, 2013, now Pat. No. 9,730,593.

(60) Provisional application No. 62/132,497, filed on Mar. 12, 2015, provisional application No. 61/882,403, filed on Sep. 25, 2013.

(51) Int. Cl.
| | |
|---|---|
| *A61B 5/024* | (2006.01) |
| *A61B 5/0245* | (2006.01) |
| *A61B 5/282* | (2021.01) |
| *A61B 5/316* | (2021.01) |
| *A61B 5/333* | (2021.01) |
| *A61B 5/339* | (2021.01) |
| *A61B 5/361* | (2021.01) |
| *A61B 5/363* | (2021.01) |
| *A61B 5/0205* | (2006.01) |
| *A61B 5/35* | (2021.01) |
| *A61B 5/259* | (2021.01) |
| *A61B 5/364* | (2021.01) |

(52) U.S. Cl.
CPC .............. *A61B 5/282* (2021.01); *A61B 5/316* (2021.01); *A61B 5/333* (2021.01); *A61B 5/339* (2021.01); *A61B 5/361* (2021.01); *A61B 5/363* (2021.01); *A61B 5/6823* (2013.01); *A61B 5/7203* (2013.01); *A61B 5/0205* (2013.01); *A61B 5/259* (2021.01); *A61B 5/35* (2021.01); *A61B 5/364* (2021.01); *A61B 5/742* (2013.01)

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,506,678 A | 3/1985 | Russell et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,788,983 A | 12/1988 | Brink et al. |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,312,446 A | 5/1994 | Holschbach et al. |
| 5,314,453 A | 5/1994 | Jeutter |
| 5,331,966 A | 7/1994 | Bennett et al. |
| 5,333,615 A | 8/1994 | Craelius et al. |
| 5,341,806 A | 8/1994 | Gadsby et al. |
| 5,348,008 A | 9/1994 | Bomn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sandford et al. |
| 5,458,141 A | 10/1995 | Neil |
| 5,473,537 A | 12/1995 | Glazer et al. |
| 5,479,922 A | 1/1996 | Reichl |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| 5,860,918 A | 1/1999 | Schradi et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,956,013 A * | 9/1999 | Raj ....................... A61B 5/339 345/208 |
| 5,957,857 A | 9/1999 | Hartley |
| 5,984,102 A | 11/1999 | Tay |
| 5,987,352 A | 11/1999 | Klein et al. |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,185,452 B1 | 2/2001 | Schulman et al. |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |

(56) References Cited

U.S. PATENT DOCUMENTS

| | | |
|---|---|---|
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |
| 6,434,410 B1 | 8/2002 | Cordero |
| 6,454,708 B1 | 9/2002 | Ferguson et al. |
| 6,456,256 B1 | 9/2002 | Amundson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,052,472 B1 | 5/2006 | Miller et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bomzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Comdorf |
| 7,552,031 B2 | 6/2009 | Vock et al. |
| D606,656 S | 12/2009 | Kobayashi et al. |
| 7,672,714 B2 | 3/2010 | Kuo et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegel et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,545,416 B1 | 10/2013 | Kayyali et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,858,432 B2 | 10/2014 | Robertson et al. |
| 8,938,287 B2 | 1/2015 | Felix et al. |
| 8,948,935 B1 | 2/2015 | Peeters |
| 8,965,492 B2 | 2/2015 | Baker et al. |
| 9,066,664 B2 | 6/2015 | Karjalainen |
| 9,135,608 B2 | 9/2015 | Herlitz |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 2001/0051766 A1 | 12/2001 | Gazdzinski |
| 2002/0013538 A1 | 1/2002 | Teller |
| 2002/0013717 A1 | 1/2002 | Ando et al. |
| 2002/0016798 A1 | 2/2002 | Sakai |
| 2002/0082867 A1 | 6/2002 | MacCarter et al. |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0149349 A1 | 8/2003 | Jensen |
| 2003/0174881 A1 | 9/2003 | Simard et al. |
| 2003/0176802 A1 | 9/2003 | Galen et al. |

(56) References Cited

U.S. PATENT DOCUMENTS

| | | |
|---|---|---|
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0043640 A1 | 2/2005 | Chang |
| 2005/0058701 A1 | 3/2005 | Gross et al. |
| 2005/0096717 A1 | 5/2005 | Bishay et al. |
| 2005/0101875 A1 | 5/2005 | Semler et al. |
| 2005/0108055 A1 | 5/2005 | Ott et al. |
| 2005/0113661 A1 | 5/2005 | Nazeri |
| 2005/0137485 A1* | 6/2005 | Cao .............. A61N 1/3622 600/510 |
| 2005/0151640 A1 | 7/2005 | Hastings |
| 2005/0154267 A1 | 7/2005 | Bardy |
| 2005/0154294 A1 | 7/2005 | Uchiyama et al. |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030781 A1 | 2/2006 | Shennib |
| 2006/0030904 A1 | 2/2006 | Quiles |
| 2006/0041201 A1 | 2/2006 | Behbehani et al. |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0111943 A1 | 5/2006 | Wu |
| 2006/0122469 A1 | 6/2006 | Martel |
| 2006/0124193 A1 | 6/2006 | Orr et al. |
| 2006/0167502 A1 | 7/2006 | Haefner |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0088419 A1 | 4/2007 | Fiorina et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0142722 A1 | 6/2007 | Chang |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0233198 A1 | 10/2007 | Ghanem et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0270678 A1 | 11/2007 | Fadem |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027337 A1 | 1/2008 | Dugan |
| 2008/0027339 A1 | 1/2008 | Nagai et al. |
| 2008/0051668 A1 | 2/2008 | Bardy |
| 2008/0058661 A1 | 3/2008 | Bardy |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0143080 A1 | 6/2008 | Burr |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0243012 A1 | 10/2008 | Fujihashi et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0177168 A1 | 12/2008 | Callahan et al. |
| 2008/0306359 A1 | 12/2008 | Zdeblick et al. |
| 2008/0309481 A1 | 12/2008 | Tanaka et al. |
| 2008/0312522 A1 | 12/2008 | Rowlandson et al. |
| 2009/0009342 A1 | 1/2009 | Karjalainen |
| 2009/0012412 A1 | 1/2009 | Wiesel |
| 2009/0012979 A1 | 1/2009 | Bateni et al. |
| 2009/0054737 A1 | 2/2009 | Magar et al. |
| 2009/0054952 A1 | 2/2009 | Glukhovsky et al. |
| 2009/0062670 A1 | 3/2009 | Sterling |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0076364 A1 | 4/2009 | Libbus et al. |
| 2009/0088652 A1 | 4/2009 | Tremblay |
| 2009/0093687 A1 | 4/2009 | Telfort et al. |
| 2009/0112116 A1 | 4/2009 | Lee et al. |
| 2009/0131759 A1 | 5/2009 | Sims et al. |
| 2009/0133047 A1 | 5/2009 | Lee et al. |
| 2009/0156908 A1 | 6/2009 | Belalcazar et al. |
| 2009/0182204 A1 | 7/2009 | Semler et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2009/0327715 A1 | 12/2009 | Smith et al. |
| 2010/0007413 A1 | 1/2010 | Herleikson et al. |
| 2010/0022897 A1 | 1/2010 | Parker et al. |
| 2010/0056877 A1 | 3/2010 | Fein et al. |

(56) References Cited

U.S. PATENT DOCUMENTS

| | | |
|---|---|---|
| 2010/0056881 A1 | 3/2010 | Libbus et al. |
| 2010/0076517 A1 | 3/2010 | Imran |
| 2010/0081913 A1 | 4/2010 | Cross et al. |
| 2010/0137694 A1 | 6/2010 | Irazoqui et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234697 A1 | 9/2010 | Walter et al. |
| 2010/0234715 A1 | 9/2010 | Shin et al. |
| 2010/0234716 A1 | 9/2010 | Engel |
| 2010/0268103 A1* | 10/2010 | McNamara ............ A61B 5/361 600/523 |
| 2010/0280366 A1 | 11/2010 | Arne et al. |
| 2010/0298720 A1 | 11/2010 | Potkay |
| 2010/0312188 A1 | 12/2010 | Robertson et al. |
| 2010/0317957 A1 | 12/2010 | Lee et al. |
| 2010/0324384 A1 | 12/2010 | Moon et al. |
| 2010/0324405 A1 | 12/2010 | Niemi et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0082842 A1 | 4/2011 | Groseclose, Jr. et al. |
| 2011/0105861 A1 | 5/2011 | Derchak et al. |
| 2011/0112379 A1 | 5/2011 | Li et al. |
| 2011/0144470 A1 | 6/2011 | Mazar et al. |
| 2011/0160548 A1 | 6/2011 | Forster |
| 2011/0160601 A1 | 6/2011 | Wang et al. |
| 2011/0208076 A1 | 8/2011 | Fong et al. |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2011/0313305 A1 | 12/2011 | Rantala |
| 2012/0003933 A1 | 1/2012 | Baker et al. |
| 2012/0029300 A1 | 2/2012 | Paquet |
| 2012/0029306 A1 | 2/2012 | Paquet et al. |
| 2012/0029309 A1 | 2/2012 | Paquest et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1* | 4/2012 | Solosko ............... A61B 5/0006 600/509 |
| 2012/0108993 A1 | 5/2012 | Gordon et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0179665 A1 | 7/2012 | Baarman et al. |
| 2012/0184207 A1 | 7/2012 | Gaines |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0265080 A1 | 10/2012 | Yu et al. |
| 2012/0265738 A1 | 10/2012 | Beckmann et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0124891 A1 | 5/2013 | Donaldson |
| 2013/0131530 A1 | 5/2013 | Brockway et al. |
| 2013/0158361 A1 | 6/2013 | Bardy |
| 2013/0172763 A1 | 7/2013 | Wheeler |
| 2013/0197380 A1 | 8/2013 | Oral et al. |
| 2013/0225963 A1 | 8/2013 | Kodandaramaiah et al. |
| 2013/0225966 A1 | 8/2013 | Barber et al. |
| 2013/0231947 A1 | 9/2013 | Shusterman |
| 2013/0243105 A1 | 9/2013 | Lei et al. |
| 2013/0274565 A1 | 10/2013 | Langer et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Barber et al. |
| 2014/0002234 A1 | 1/2014 | Alwan |
| 2014/0005502 A1 | 1/2014 | Klap et al. |
| 2014/0012154 A1 | 1/2014 | Mazar et al. |
| 2014/0031663 A1 | 1/2014 | Gallego |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0121557 A1 | 5/2014 | Gannon et al. |
| 2014/0140359 A1 | 5/2014 | Kalevo et al. |
| 2014/0148718 A1* | 5/2014 | Stickney ............ A61N 1/36592 600/523 |
| 2014/0180027 A1 | 6/2014 | Buller |
| 2014/0189928 A1 | 7/2014 | Oleson et al. |
| 2014/0194760 A1 | 7/2014 | Albert |
| 2014/0206977 A1 | 7/2014 | Bahney et al. |
| 2014/0213937 A1 | 7/2014 | Bianchi et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0296651 A1 | 10/2014 | Stone |
| 2014/0297310 A1 | 10/2014 | Collins |
| 2014/0318699 A1 | 10/2014 | Longinotti-Buitoni et al. |
| 2014/0330147 A1* | 11/2014 | Ousdigian .......... A61N 1/37235 600/509 |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0018660 A1 | 1/2015 | Thomson et al. |
| 2015/0048836 A1 | 2/2015 | Guthrie et al. |
| 2015/0051472 A1 | 2/2015 | Wang et al. |
| 2015/0065842 A1 | 3/2015 | Lee et al. |
| 2015/0094558 A1 | 4/2015 | Russell |
| 2015/0142090 A1 | 5/2015 | Duijsens et al. |
| 2015/0164349 A1 | 6/2015 | Gopalakrishnan et al. |
| 2015/0165211 A1 | 6/2015 | Naqvi et al. |
| 2015/0177175 A1 | 6/2015 | Elder et al. |
| 2015/0202351 A1 | 7/2015 | Kaplan et al. |
| 2015/0250422 A1 | 9/2015 | Bay |
| 2015/0257670 A1 | 9/2015 | Ortega et al. |
| 2015/0305676 A1 | 11/2015 | Shoshani |
| 2015/0324690 A1 | 11/2015 | Chilimbi et al. |
| 2015/0335285 A1 | 11/2015 | Poon et al. |
| 2015/0359489 A1 | 12/2015 | Baudenbacher et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0196479 A1 | 7/2016 | Chertok et al. |
| 2016/0217369 A1 | 7/2016 | Annapureddy et al. |
| 2016/0217691 A1 | 7/2016 | Kadobayashi et al. |

(56) References Cited

U.S. PATENT DOCUMENTS

| | | |
|---|---|---|
| 2016/0235318 A1 | 8/2016 | Sarkar |
| 2016/0150982 A1 | 9/2016 | Roy |
| 2017/0056650 A1 | 3/2017 | Cohen et al. |
| 2017/0065207 A1 | 3/2017 | Landherr et al. |
| 2017/0112399 A1 | 4/2017 | Brisben et al. |
| 2017/0112401 A1 | 4/2017 | Rapin et al. |
| 2017/0127964 A1 | 5/2017 | Moorman |
| 2017/0156592 A1 | 6/2017 | Fu |
| 2017/0032221 A1 | 7/2017 | Wu et al. |
| 2017/0281032 A1 | 10/2017 | Weinberg et al. |
| 2017/0281033 A1 | 10/2017 | Higgins et al. |
| 2017/0354365 A1 | 12/2017 | Zhou |
| 2017/0366921 A1 | 12/2017 | Pflugh et al. |
| 2018/0020931 A1 | 1/2018 | Shusterman |
| 2018/0042552 A1 | 2/2018 | Li et al. |
| 2018/0078771 A1 | 3/2018 | Koop et al. |
| 2018/0116537 A1 | 5/2018 | Sullivan et al. |
| 2018/0129893 A1 | 5/2018 | Son et al. |
| 2018/0192965 A1 | 7/2018 | Rose et al. |
| 2018/0264258 A1 | 9/2018 | Cheng et al. |
| 2018/0333058 A1 | 11/2018 | Coulon et al. |
| 2019/0021671 A1 | 1/2019 | Kumar et al. |
| 2019/0046038 A1 | 2/2019 | Weinstein et al. |
| 2019/0059763 A1 | 2/2019 | Shakur et al. |
| 2019/0069815 A1 | 3/2019 | Burnes et al. |
| 2019/0117068 A1 | 4/2019 | Thomson et al. |
| 2019/0336032 A1 | 11/2019 | Gill et al. |
| 2020/0038671 A1 | 2/2020 | Schulhauser et al. |
| 2020/0352441 A1 | 11/2020 | Soykan et al. |

FOREIGN PATENT DOCUMENTS

| | | | |
|---|---|---|---|
| JP | H11188015 | 7/1999 | |
| JP | 2004129788 | 4/2004 | |
| JP | 2007082938 | 4/2007 | |
| JP | 2009219554 | 10/2009 | |
| WO | 199852463 | 11/1998 | |
| WO | 00/78213 | 12/2000 | |
| WO | 2003032192 | 4/2003 | |
| WO | 2006009767 | 1/2006 | |
| WO | 2006014806 | 2/2006 | |
| WO | 2007066270 | 6/2007 | |
| WO | 2007092543 | 8/2007 | |
| WO | 2008010216 | 1/2008 | |
| WO | 2008057884 | 5/2008 | |
| WO | 2008092098 | 7/2008 | |
| WO | 2009036306 | 3/2009 | |
| WO | 2009036313 | 3/2009 | |
| WO | 2009036327 | 3/2009 | |
| WO | 2009112976 | 9/2009 | |
| WO | 2009112978 | 9/2009 | |
| WO | 2009112979 | 9/2009 | |
| WO | 2009142975 | 11/2009 | |
| WO | 2010066507 | 6/2010 | |
| WO | 2010104952 | 9/2010 | |
| WO | 2010105045 | 9/2010 | |
| WO | 2011047207 | 4/2011 | |
| WO | 2012040487 | 3/2012 | |
| WO | WO-2012040487 A1 * | 3/2012 | ............. A61B 5/042 |
| WO | 2012112407 | 8/2012 | |
| WO | 2012140559 | 10/2012 | |
| WO | 2012146957 | 11/2012 | |
| WO | 2017072250 | 5/2017 | |
| WO | 2019030746 | 2/2019 | |
| WO | 2019073288 | 4/2019 | |

OTHER PUBLICATIONS

Pourbabaee Bahareh et al. "Feature Learning with Deep Convolutional Neural Networks for Screening Patients with Paroxysmal Atrial Fibrillation," 2016 Neural Networks (IJCNN), 2016 International Joint Conference on Neural Networks (IJCNN), IEEE, Jul. 24, 2016 (Jul. 24, 2016), pp. 5057-5064, XP032992832, DOI: 10.1109/IJCNN.2016.7727866.

Xiong Zhaohan et al. "Robust ECG Signal Classification for Detection of Atrial Fibrillation Using a Novel Neural Network," 2017 Computing in Cardiology (CinC), CCAL, Sep. 24, 2017 (Sep. 24, 2017), pp. 1-4, XP033343575, DOI: 10.22489/CinC.2017.066-138.

Wallot et al., "Using Complexity Metrics With R-R Intervals And BPM Heart Rate Measures," Frontiers in Physiology, vol. 4, Article 211, pp. 1-8, Aug. 13, 2013. 2013.

https://www.meddeviceonline.com/doc/medtronic-launches-world-s-first-app-based-remote-monitoring-system-for-pacemakers-0001. Nov. 18, 2015.

https://fccid.io/LF524950/User-Manual/User-Manual-1944573 © Medtronic, Inc. 2012.

https://en.wikipedia.org/wiki/Convolutional_neural_network#Receptive_fields_in_the_visual_cortex (Year: 2017).

Dan Sapoznikov et al., "Comparison of Different Methodologies of Heart Rate Variability Analysis," Department of Cardiology, Hadassah University Hospital, P.O.B. 12000, Ein Kerem, Jerusalem 91120, Israel (1993).

Jeffrey J. Goldberger, MD, FHRS, et al., "Comparison of the Physiologic and Prognostic Implications of the Heart Rate Versus the RR Interval," Heart Rhythm, Elseview, US, vol. 11, No. 11, Jul. 30, 2014 (Jul. 30, 2014), pp. 1925-1933, XP029082764, ISSN: 1547-5271, DOI: 10.1016/J.HRTHM.2014.07.037 (2014).

Giuseppe Ciconte et al., "The Role Of Implantable Cardiac Monitors In Artial Fibrillation Management," Journal For Atrial Finrillation: JAFIB, vol. 10, No. 2, Aug. 31, 2017 (Aug. 31, 2017), XPO55732155, ISSN: 1941-6911, DOI: 10.4022/iafib. 1590. Aug. 31, 2017.

BioMonitor 2 Cardiac Monitor With Fast Insert Tools BIOTRONIK Home Monitoring, BioMonitor 2—technical manual, Jul. 6, 2017 (Jul. 6, 2017), pp. 1-29, XPO55732157, [retrieved on Sep. 18, 2020].

"RevealLINQ Product Specifications," Dec. 1, 2017 (Dec. 1, 2017), XPO55732158, [retrieved on Sep. 18, 2020].

Helmut Purerfellner et al.: "Miniaturized Reveal LINQ insertable cardiac monitoring system: First-in-human experience," Heart Rhythm, vol. 12. No 6, Jun. 1, 2015 (Jun. 1, 2015), pp. 1113-1119, XP055732303, US ISSN 1547-5271, DOI: 10.1016/j.hrthm.2015.02.030.

Dwayne C. Leonard, A Framework for the Creation of a Unified Electronic Medical Record Using Biometrics, Data Fusion and Belief Theory, 2007, https://dialog.proquest.com/professional/docview/304852676/17AEEF1F9382EF1C4E5/6?accountid=131444 (last visited Aig 27, 2021) (Year: 2007).

15 Of The Hottest Wearable Gadgets, URL <http://thehottestgadgets.com/2008/09/the-15-hottest-wearable-gadgets-001253> (Web page cached on Sep. 27, 2008).

Alivecor, URL <http://www.businesswire.eom/news/home/20121203005545/en/AliveCor%E2%80%99s-Heart-Monitor-Phone-Receives-FDA-Clearance#.U7rtq7FVTyF> (Dec. 3, 2012).

Bharadwaj et al.. Techniques for Accurate ECG signal processing, EE Times, URL <www.eetimes.com/document.asp?doc_id=1278571> (Feb. 14, 2011).

Chen et al. "Monitoring Body Temperature of Newborn Infants At Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.).

Smith, Jawbone Up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am Coll. Cardiol; 2007; 49; 1109-27, 75 Pgs.

Lauren Gravitz, "When Your Diet Needs A Band-Aid,"Technology Review, MIT. (May 1, 2009).

Lieberman, Jonathan, "How Telemedicine Is Aiding Prompt ECG Diagnosis In Primary Care," British Journal of Community Nursing,

(56) References Cited

OTHER PUBLICATIONS vol. 13, No. 3, Mar. 1, 2008 (Mar. 1, 20081), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013.).

Nike+ Fuel Band, URL <http://www.nike.com/US/en_us/c/nikeplus-fuelband> (Web page cached on Jan. 11, 2013.).

P. Libby et al.,"Braunwald's Heart Disease—A Textbook of Cardiovascular Medicine," Chs. 11, pp. 125-148 and 12, pp. 149-193 (8th ed. 2008), American Heart Association.

Initial hands-on with Polar Loop activity tracker, URL <http://www.dcrainmaker.com/2013/09/polar-loop-firstlook.html> (Sep. 17, 2013).

Seifert, Dan, Samsung dives into fitness wearable with the Gear Fit/ The Verge, URL <http://www.theverge. com/2014/2/24/5440310/samsung-dives-into-fitness-wearables-with-the-gear-fit> (Feb. 24, 2014).

Soper, Taylor, Samsung's new Galaxy S5 flagship phone has fingerprint reader, heart rate monitor, URL <http://www.geekwire.com/2014/samsung-galaxy-s5-fingerprint> (Feb. 24, 2014).

Dolcourt, See the Samsung Galaxy S5's Heart rate monitor in action, URL <http://www.cnet.com/news/see-the-samsung-galaxy-s5s-heart-rate-monitor-in-action> (Feb. 25, 2014).

Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.

Sleepview, URL <http://www.clevemed.com/sleepview/overview.shtml> (Web page cached on Sep. 4, 2013.).

Actigraphy/ Circadian Rhythm SOMNOwatch, URL <http://www.somnomedics.eu/news-events/publications/somnowatchtm.html> (Web page cached on Jan. 23, 2010).

Zio Event Card, URL <http://www.irhythmtech.com/zio-solution/zio-event/> (Web page cached on Mar. 11, 2013.).

Zio Patch System, URL <http://www.irhythmtech.com/zio-solution/zio-system/index.html> (Web page cached on Sep. 8, 2013.).

Saadi et al. "Heart Rhythm Analysis Using ECG Recorded With A Novel Sternum Based Patch Technology—A Pilot Study." Cardio technix 2013—Proceedings of the International Congress on Cardiovascular Technologies, Sep. 20, 2013.

Anonymous. Omegawave Launches Consumer App 2.0 in U.S. "Endurance Sportswire—Endurance Sportswire." Jul. 11, 2013. URL:http://endurancesportswire.com/omegawave-launches-consumer-app-2-0-in-u-s/.

Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society. Jul. 1, 2013.

Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.

Daoud et al. "Fall Detection Using Shimmer Technology And Multiresolution Analysis." Aug. 2, 2013. URL: https://decibel.ni.com/content/docs/DOC-26652.

Libbus. "Adherent Cardiac Monitor With Wireless Fall Detection For Patients With Unexplained Syncope." Abstracts of the First AMA-IEEE Medical Technology Conference On Individualized Healthcare. May 22, 2010.

Duttweiler et al., "Probability Estimation In Arithmetic And Adaptive-Huffman Entropy Coders," IEEE Transactions an Image Processing. vol. 4, No. 3, Mar. 1, 1995, pp. 237-246.

Gupta et al., "An ECG Compression Technique For Telecardiology Application," India Conference (INDICON), 2011 Annual IEEE, Dec. 16, 2011, pp. 1-4.

Nave et al., "ECG Compression Using Long-Term Prediction," IEEE Transactions on Biomedical Engineering, IEEE Service Center, NY, USA, vol. 40, No. 9, Sep. 1, 1993, pp. 877-885.

Skretting et al., "Improved Huffman Coding Using Recursive Splitting," NORSIG, Jan. 1, 1999.

A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/j.1399-5618.2006.00364.x.

Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].

Vedapulse UK, Jan. 1, 2014 (Jan. 1, 2014), XP002757887, Retrieved from the Internet: URL:http://www.vedapulseuk.com/diagnostic/ [retrieved on May 19, 2016].

http://www.originlab.com/origin#Data_Exploration 2015.

https://web.archive.org/web/20130831204020/http://www.biopac.com/research.asp?CatID=37&Main=Software (Aug. 2013).

ADINSTRUMENTS:ECG Analysis Module For LabChart & PowerLab, 2008.

BIOPAC Systems, Inc. #AS148-Automated ECG Analysis , Mar. 24, 2006.

Health Research—Hexoskin Biometric Shirt | Hexoskin URL:http://www.hexoskin.com/pages/health-research (Web page cached on Dec. 2, 2014).

Jacob Kastrenakes, "Apple Watch uses four sensors to detect your pulse," Sep. 9, 2014. URL: http://www.theverge.com/2014/9/9/6126991/apple-watch-four-back-sensors-detect-activity.

Nicole Lee, "Samsung Gear S review: an ambitious and painfully flawed smartwatch," Dec. 1, 2014. URL http://www.engadget.com/2014/12/01/samsung-gear-s-review/.

G. G. Ivanov, "HRV Analysis Under The Usage Of Different Electrocardiopraphy Systems," Apr. 15, 2008 (Apr. 15, 2008), XP55511209, Retrieved from the Internet: URL:http://www.drkucera.eu/upload_doc/hrv_analysis_ methodical_recommendations).pdf [retrieved on Oct. 1, 2018].

http://www.gtec.at/Products/Software/g.BSanalyze-Specs-Features (2014).

May 24, 2022 Letter to Opposing Counsel. 1:22-cv-00351-CFC. May 24, 2022.

Complaint from Case No. 1:22-cv-00351-UNA, *Bardy Diagnostics, Inc.* (Plaintiff) v. *Vital Connect, Inc.* (Defendant), Filed: Mar. 18, 2022, 182 pages.

Defendant's Opening Brief In Support of Its Motion To Dismiss For Failure to State A Claim from Case No. 1:22-cv-00351-CFC, *Bardy Diagnostics, Inc.* (Plaintiff) v. *Vital Connect, Inc.* (Defendant), Filed: May 25, 2022, 18 pages.

Defendant's Answer, Defenses, and Counterclaim from Case No. 1:22-cv-00351-CFC, *Bardy Diagnostics, Inc.* (Plaintiff) v. *Vital Connect, Inc.* (Defendant), Filed: May 25, 2022, 132 pages.

Plaintiff's Answering Brief In Opposition to Defendant's Motion to Dismiss For Failure to State a Claim from Case No. 1:22-cv-00351-CFC, *Bardy Diagnostics, Inc.* (Plaintiff) v. *Vital Connect, Inc.* (Defendant), Filed: Jun. 8, 2022, 25 pages.

Plaintiff's Answer to Defendant's Counterclaim from Case No. 1:22-cv-00351-CFC, *Bardy Diagnostics, Inc.* (Plaintiff) v. *Vital Connect, Inc.* (Defendant), Filed: Jun. 15, 2022, 5 pages.

Defendant's Reply Brief In Support of Its Motion to Dismiss For Failure to State a Claim from Case No. 1:22-cv-00351-CFC, *Bardy Diagnostics, Inc.* (Plaintiff) v. *Vital Connect, Inc.* (Defendant), Filed: Jun. 15, 2022, 93 pages.

May 2, 2022 Letter From Counsel. 1:22-cv-00351-CFC. May 2, 2022.

Oct. 17, 2022 Letter to Opposing Counsel, *Bardy Diagnostics, Inc.* v. *Vital Connect, Inc.*, No. 22-cv-00351-CFC (D. Del.), Oct. 17, 2022.

Nov. 11, 2022, Letter from Opposing Counsel, 1:22-cv-00351-CJB; *Bardy Diagnostics, Inc.* v. *Vital Connect, Inc.* (D. Del.), Nov. 11, 2022.

Dec. 26, 2022 Letter from Opposing Counsel, 1:22-cv-00351-CJB; *Bardy Diagnostics, Inc.* v. *Vital Connect, Inc.* (D. Del.); and IPR2023-00381; *Vital Connect, Inc.* v. *Bardy Diagnostics, Inc.* (P.T.A.B.), Dec. 26, 2022.

First Amended Complaint for Patent Infringement, 1:22-cv-00351-CJB, *Bardy Diagnostics, Inc.* v. *Vital Connect, Inc.* (D. Del.), filed Jan. 10, 2023.

(56) References Cited

OTHER PUBLICATIONS

Petition for Inter Partes Review of U.S. Pat. No. 11,051,743 Pursuant To 35 U.S.C. §§ 311-319 and 37 C.F.R. § 42, Case No. IPR2023-00381, *Vital Connect, Inc.* v. *Bardy Diagnostics, Inc.* (P.T.A.B.), Dec. 21, 2022, 875 pages.
Defendant's Answer to First Amended Complaint, Defenses, and Counterclaim, 1:22-cv-00351-CJB, *Bardy Diagnostics, Inc.* v. *Vital Connect, Inc.* (D. Del.), filed Jan. 24, 2023 (227 pages).

\* cited by examiner

CAM Report

Patient Data
Patient Name
Patient ID
Age 40
Sex Male
Indication Atrial fibrillation
Pacemaker ■
Notes Physician Robert Rho MD
Organization Evergreen Health
CAM ID 0JWG-U73W6

Report Summary
Recording Length 6 days, 23 hours
Recording Period Aug 19 10:45:00am
Aug 26 09:59:27am Button Presses Count 21
Correlate to: AF, AT, NSR, PAC, PVC
Count 13
Diary Entries Correlate to: AF, AFL, AT, NSR, PAC, PVC, ST Critical Status Notes
None Physician Interpretation

Major Preliminary Findings
There were several brief and a couple sustained periods of atrial fibrillation/atrial flutter. The longest sustained period lasted 15.7 hours. Periods of AF had primarily moderate control.
However, rapid AF/AFL totaled 6.4 hours. Periods of AFL were primarily 2:1 conduction, along with intermittent periods of variable condition.
- There were 20 asystole pauses during AF; the longest was 3.3 seconds
-4 brief runs VT; the longest/fastest was 4 beats @ 200 bpm

ECG Analysis Summary
Impulse Formation & Conduction
Dominant Rhythm NSR, EAR
Avg 68 bpm
Heart Rates Min 47 bpm
Max 156 bpm
PR 0.19 s  ☐ 1" AV Block
QRS 0.10 s  ☐ BBB
ECG Intervals QT 0.36 s  ☐ Prolonged
QTC 0.39 s Pacer ☐
Sinus P-Wave ☐
EAR ■
ST ■ 33%>100 bpm
SB ☐
SA ☐
Sinus Exit Block ☐
Junctional ■
IVR ☐
AV Block ☐
Pauses ■ Episodes 20 > 2.5 s
Longest 3.3 s Supraventricular Arrhythmias
AF ■ Episodes 4  Avg 93 bpm
Burden 11.2%  Min 46 bpm
Longest 15.7 h  Max 176bpm AFL ■ Episodes 1
Burden 3.9%
Longest 6.4 h
2:1

AT ■ Episodes 2
Longest 6 beats @ 134 bpm
Fastest 4 beats @ 227 bpm
AVNRT ☐
AVRT ☐
PAC ■ < 1% - <1000 / day
Non-conducted Ventricular Arrhythmias
VT ■ Episodes 4
Longest 4 beats @ 200 bpm
Fastest 4 beats @ 200 bpm
PVC ■ < 1% - <1000 / day
Unifocal Other
Other ■

SYSTEM AND METHOD FOR FACILITATING A CARDIAC RHYTHM DISORDER DIAGNOSIS WITH THE AID OF A DIGITAL COMPUTER

CROSS-REFERENCE TO RELATED APPLICATIONS

This non-provisional patent application is continuation of U.S. Pat. No. 11,179,087, issued Nov. 23, 2021, which is a continuation of U.S. Pat. No. 10,799,137, issued Oct. 13, 2020; which is a continuation-in-part of U.S. Pat. No. 10,736,532, issued Aug. 11, 2020; which is a continuation of U.S. Pat. No. 10,045,709, issued Aug. 14, 2018; which is a continuation of U.S. Pat. No. 9,408,551, issued Aug. 9, 2016; which is a continuation-in-part of U.S. Pat. No. 9,345,414, issued May 24, 2016; which is a continuation-in-part of U.S. Pat. No. 9,408,545, issued Aug. 9, 2016; which is a continuation-in-part of U.S. Pat. No. 9,700,227, issued Jul. 11, 2017; which is a continuation-in-part of U.S. Pat. No. 9,730,593, issued Aug. 15, 2017, and further claims priority under 35 U.S.C. § 119(e) to U.S. Provisional Patent Application, Ser. No. 62/132,497, filed Mar. 12, 2015, and U.S. Provisional Patent Application, Ser. No. 61/882,403, filed Sep. 25, 2013, the disclosures of which are incorporated by reference.

FIELD

This application relates in general to electrocardiographic monitoring and, in particular, to a method for facilitating diagnosis of cardiac rhythm disorders with the aid of a digital computer.

BACKGROUND

An electrocardiogram (ECG) allows physicians to diagnose cardiac function by visually tracing the cutaneous electrical signals (action potentials) that are generated by the propagation of the transmembrane ionic currents that trigger the depolarization of cardiac fibers. An ECG trace contains alphabetically-labeled waveform deflections that represent distinct features within the cyclic cardiac activation sequence. The P-wave represents atrial depolarization, which causes atrial contraction. The QRS-complex represents ventricular depolarization. The T-wave represents ventricular repolarization.

The R-wave is often used as an abbreviation for the QRS-complex. An R-R interval spans the period between successive R-waves and, in a normal heart, is 600 milliseconds (ms) to one second long, which respectively correspond to 100 to 60 beats per minute (bpm). The R-wave is the largest waveform generated during normal conduction and represents the cardiac electrical stimuli passing through the ventricular walls. R-R intervals provide information that allows a physician to understand at a glance the context of cardiac rhythms both before and after a suspected rhythm abnormality and can be of confirmational and collaborative value in cardiac arrhythmia diagnosis and treatment.

Conventionally, the potential of R-R interval context has not been fully realized, partly due to the difficulty of presentation in a concise and effective manner to physicians. For instance, routine ECGs are typically displayed at an effective paper speed of 25 millimeters (mm) per second. A lower speed is not recommended because ECG graph resolution degrades at lower speeds and diagnostically-relevant features may be lost. Conversely, a half-hour ECG recording, progressing at 25 mm/s, results in 45 meters of ECG waveforms that, in printed form, is cumbersome and, in electronic display form, will require significant back and forth toggling between pages of waveforms, as well as presenting voluminous data transfer and data storage concerns. As a result, ECGs are less than ideal tools for diagnosing cardiac arrhythmia patterns that only become apparent over an extended time frame, such as 30 minutes or longer.

R-R intervals have also been visualized in Poincare plots, which graph RR(n) on the x-axis and RR(n+1) on the y-axis. However, a Poincare plot fails to preserve the correlation between an R-R interval and the R-R interval's time of occurrence and the linearity of time and associated contextual information, before and after a specific cardiac rhythm, are lost. In addition, significant changes in heart rate, particularly spikes in heart rate, such as due to sinus rhythm transitions to atrial flutter or atrial fibrillation, may be masked or distorted in a Poincare plot if the change occurs over non-successive heartbeats, rather than over two adjacent heartbeats, which undermines reliance on Poincare plots as dependable cardiac arrhythmia diagnostic tools. Further, Poincare plots cannot provide context and immediate temporal reference to the actual ECG, regardless of paper speed. Events both prior to and after a specific ECG rhythm can provide key clinical information disclosed in the R-R interval plot that may change patient management above and beyond the specific rhythm being diagnosed.

Cardiac patients can require full time monitoring, such as via a dermal or implantable cardiac device. Currently, a single cardiac device can record data over a period of 7 to 14 days, or more, before charging or data offload is required. Once offloaded, the cardiac data can be processed for providing to a physician or other medical professional for diagnosis of the patient. However, the large amounts of data collected over time are often difficult or not possible to display using current software to provide the diagnosing medical professional with the "complete picture" of the cardiac environment of the patient, including abnormal heart beats and rhythm patterns. Further, viewing the "complete picture" allows other medical professionals to easily spot and remove noise from the cardiac data.

Therefore, a need remains for presenting R-R interval data to physicians to reveal temporally-related patterns as an aid to rhythm abnormality diagnosis. Preferably, the presentation allows a physician or other medical professional to visualize an entire data set, recorded over a period of time, to obtain a complete picture of a patient's cardiac situation, to diagnose a patient or remove noise.

SUMMARY

R-R interval data is presented to physicians in a format that includes views of relevant near field and far field ECG data, which together provide contextual information that improves diagnostic accuracy. The near field (or short duration) ECG data view provides a "pinpoint" classical view of an ECG at traditional recording speed in a manner that is known to and widely embraced by physicians. The near field ECG data is coupled to a far field (or medium duration) ECG data view that provides an "intermediate" lower resolution, pre- and post-event contextual view.

Both near field and far field ECG data views are temporally keyed to an extended duration R-R interval data view. In one embodiment, the R-R interval data view is scaled non-linearly to maximize the visual differentiation for frequently-occurring heart rate ranges, such that a single glance allows the physician to make a diagnosis. All three views are presented simultaneously, thereby allowing an interpreting physician to diagnose rhythm and the pre- and post-contextual events leading up to a cardiac rhythm of interest.

The durations of the classical "pinpoint" view, the pre- and post-event "intermediate" view, and the R-R interval plot are flexible and adjustable. In one embodiment, a temporal point of reference is identified in the R-R interval plot and the ECG data that is temporally associated with the point of reference is displayed in the near field and far field ECG data views. In a further embodiment, diagnostically relevant cardiac events can be identified as the temporal point of reference. For clarity, the temporal point of reference will generally be placed in the center of the R-R interval data to allow pre- and post-event heart rhythm and ECG waveform data to present in the correct context. Thus, the pinpoint "snapshot" and intermediate views of ECG data with the extended term R-R interval data allow a physician to comparatively view heart rate context and patterns of behavior prior to and after a clinically meaningful arrhythmia, patient concern or other indicia, thereby enhancing diagnostic specificity of cardiac rhythm disorders and providing physiological context to improve diagnostic ability.

Further, providing a medical professional with a complete view of a patient's cardiac data collected over time, allows a professional to easily identify noise, as well as abnormal heart beats and rhythm patterns, which may be indicative of a cardiac condition. Additionally, snippets of the data can be collected from the complete picture, such as those representing the abnormal rhythm patterns for providing a different medial professional with a summary view of the patient's cardiac environment.

One embodiment provides a system and method for facilitating a cardiac rhythm disorder diagnosis with the aid of a digital computer. A download station retrieves cutaneous action potentials of a patient recorded over time by an ECG device as ECG data. An R-R interval plot of the ECG data includes R-R intervals plotted along an x-axis of the plot and heart rates associated with the R-R intervals plotted along a y-axis of the plot. The R-R intervals are calculated as a difference between recording times of successive pairs of R-wave peaks. Each heart rate is associated with each time difference. One or more portions of the R-R intervals are identified in the plot. Each portion of the R-R intervals includes a cardiac event. Report strips are generated and each includes one portion of the R-R intervals and a portion of the ECG data spanning a shorter duration than that portion of the R-R intervals.

The foregoing aspects enhance the presentation of diagnostically relevant R-R interval data, reduce time and effort needed to gather relevant information by a clinician and provide the clinician with a concise and effective diagnostic tool, which is critical to accurate arrhythmia and cardiac rhythm disorder diagnoses. A further embodiment provides a system for facilitating a cardiac rhythm disorder diagnosis with the aid of a digital computer. A download station is adapted to retrieve cutaneous action potentials of a patient recorded over a set period of time by an ECG monitoring and recording device as ECG data. An R-R interval plot of the ECG data includes R-R intervals plotted along an x-axis of the plot and heart rates associated with the R-R intervals plotted along a y-axis of the plot. The R-R intervals are calculated as a difference between recording times of successive pairs of R-wave peak and each heart rate is associated with each time difference. One or more portions of the R-R intervals are identified in the plot as a run with a cardiac event by marking a start and an end of each portion of the R-R intervals. One or more report strips are generated and each report strip includes one of the runs and a portion of the ECG data spanning a shorter duration than the run. The report strips are collected for inclusion in a cardiac report.

A still further embodiment provides a system for facilitating a cardiac rhythm disorder diagnosis. A download station is adapted to retrieve cutaneous action potentials of a patient recorded as ECG data. A plot of R-R interval data is generated based on the ECG data and displayed. A presentation of the R-R interval data in the display is changed by identifying a section of the R-R interval data and removing portions of the R-R interval data associated with an earlier recordation time than the R-R interval data in the section and a later recordation time than the R-R interval data in the section. The R-R interval data remaining in the display is provided in greater detail. Report strips are generated from the remaining R-R interval data and classified with a cardiac condition of the patient.

Custom software packages have been used to identify diagnostically relevant cardiac events from the electrocardiography data, but usually require a cardiologist's diagnosis and verification. In contrast, when presented with a machine-identified event, the foregoing approach aids the cardiologist's diagnostic job by facilitating presentation of ECG-based background information prior to and after the identified event.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, including time and clustering of events, all without departing from their spirit and the scope. Accordingly, the drawings and detailed description are to be regarded as illustrative in nature and not as restrictive.

BRIEF DESCRIPTION OF THE DRAWINGS

FIG. 17 is a diagram showing, by way of example, an interactive user interface for generating a run of data.

FIG. 27 is a diagram of an interactive user interface for displaying data for inclusion in a patient report.

FIG. 28 is a view of a patient report.

FIGS. 29-31 are diagrams showing, the report of FIG. 28 in further detail.

DETAILED DESCRIPTION

A normal healthy cardiac cycle repeats through an expected sequence of events that can be visually traced through an ECG. Each cycle starts with cardiac depolarization originating high in the right atrium in the sinoatrial (SA) node before spreading leftward towards the left atrium and inferiorly towards the atrioventricular (AV) node. After a delay in the AV node, the depolarization impulse transits the Bundle of His and moves into the right and left bundle branches and Purkinje fibers to activate the right and left ventricles.

Figure 1:
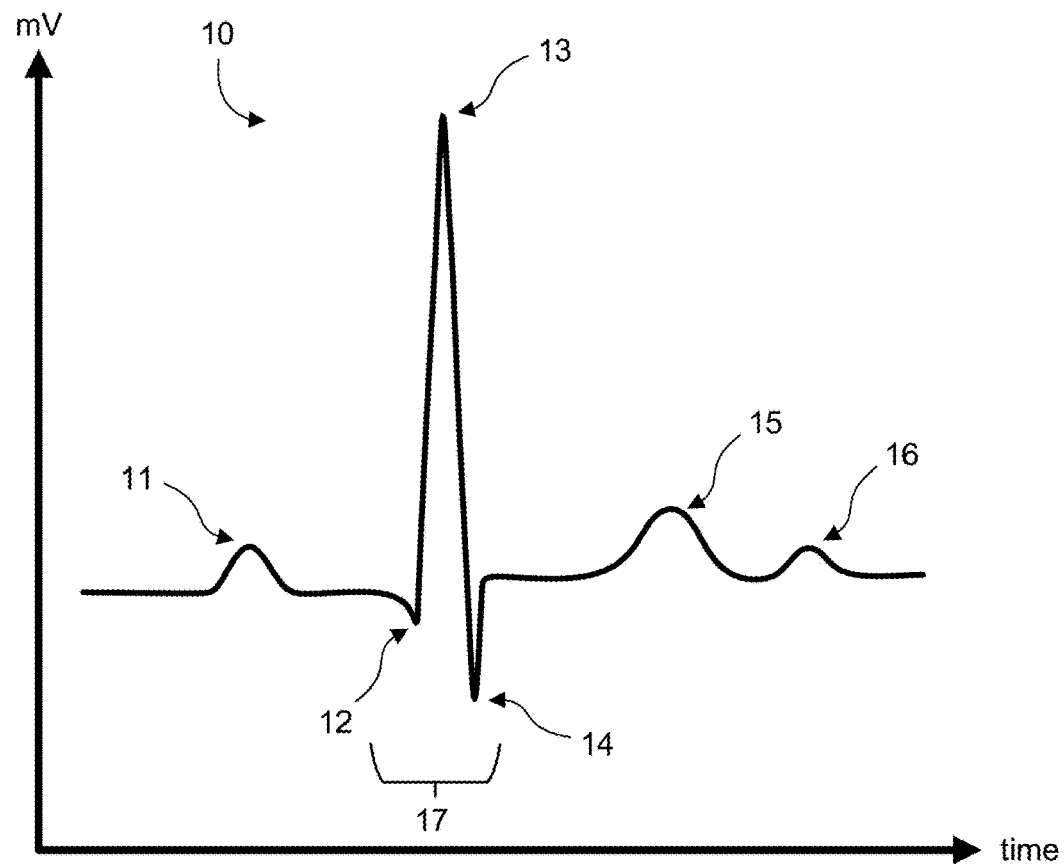
FIG. 1 is a graph showing, by way of example, a single ECG waveform.

When a rhythm disorder is suspected, diagnostically-relevant arrhythmic events in the cardiac cycle can often be identified and evaluated with the assistance of an ECG and R-R interval tachography, such as Poincaré plots. Routine ECG evaluation is primarily focused identifying changes to expected ECG waveform shapes. FIG. 1 is a graph showing, by way of example, a single ECG waveform 10. The x-axis represents approximate time in units of tenths of a second and the y-axis represents approximate cutaneous electrical signal strength in units of millivolts. By long-standing convention, ECGs are typically printed or displayed at an effective paper speed of 25 millimeters (mm) per second. Although in practice an ECG may be provided to a physician in traditional paper-printed form, in "virtual" electronic display form, or both, the term "effective paper speed" is nevertheless still widely applied as a metric to normalize the recorded ECG signal to a standardized grid of 1 mm squares (omitted for the sake of clarity in FIG. 1), whereby each 1 mm horizontal box in the grid corresponds to 0.04 s (40 ms) of recorded time. Other effective paper speeds, grid sizes and units of display are possible.

A full ECG consists of a stream of alphabetically-labeled waveforms 10 that collectively cover cardiac performance over a period of observation. For a healthy patient, within each ECG waveform 10, the P-wave 11 will normally have a smooth, normally upward, positive waveform that indicates atrial depolarization. The QRS complex 17 will usually follow, often with a downward deflection of a Q-wave 12, followed by a larger upward deflection of an R-wave 13, and be terminated with a downward waveform of the S-wave 14, which are collectively representative of ventricular depolarization. The T-wave 15 will normally be a modest upward waveform, representative of ventricular repolarization, while the U-wave 16, which is often not directly observable, will indicate the recovery period of the Purkinje conduction fibers.

Rhythm disorders often manifest through R-R interval variability and the patterns formed by R-R intervals over an extended time period are important tools in the diagnosis of cardiac rhythm abnormalities. For example, atrial fibrillation (AF) is the chaotic firing of the atria that leads to an erratic activation of the ventricles. AF is initially diagnosed by an absence of organized P-waves 11 and confirmed by erratic ventricular rates that manifest in an ECG R-R interval plot as a cloud-like pattern of irregular R-R intervals due to an abnormal conduction of impulses to the ventricles. There is a Gaussian-like distribution to these R-R intervals during AF. Similarly, atrial flutter (AFL) is an abnormal heart rhythm in which cardiac impulses travel along pathways within the right atrium in an organized circular motion, causing the atria to beat faster than and out of sync with the ventricles. During AFL, the heart beats quickly, yet with a regular pattern. Although AFL presents in an electrogram (e-gram) as a "sawtooth" pattern, AFL can be confirmed in an ECG by characteristic R-R interval patterns that usually manifest as 2:1 atrioventricular (AV) conduction or 4:1 atrioventricular conduction. On occasion, the conduction through the AV node is variable and not fixed.

Figure 2:
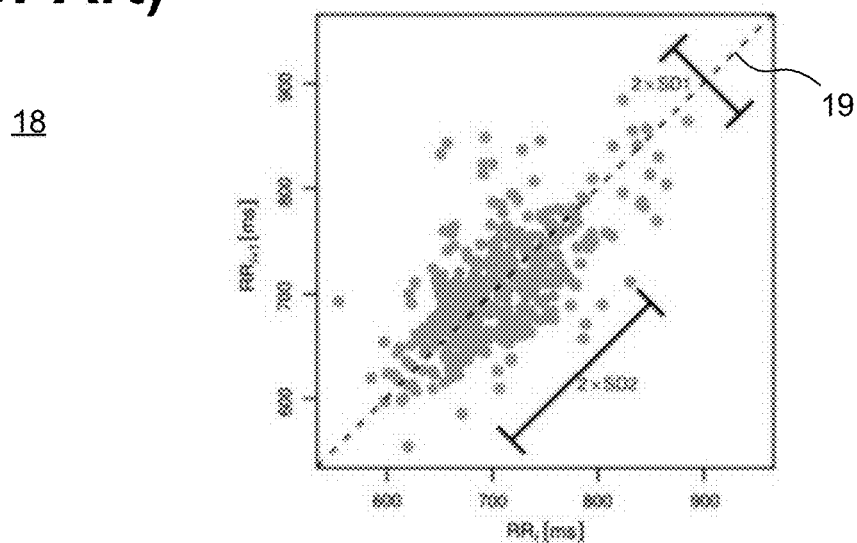
FIG. 2 is a graph showing, by way of example, a prior art Poincaré R-R interval plot.

Conventionally, R-R intervals have been visualized using Poincare plots. FIG. 2 is a graph showing, by way of example, a prior art Poincare R-R interval plot 18. The x-axis represents the duration of R-R interval n in units of milliseconds (ms). The y-axis represents the duration of R-R interval n+1 also in units of ms. Ordinarily, the x- and y-axes use the same units, so as to form a trend line 19 along the 45-degree angle. When an R-R interval is equal to the successive R-R interval, as often occurs when heart rhythm is regular, the dot representing the two intervals falls onto the 45-degree trend line 19. Conversely, when an R-R interval has changed since the preceding R-R interval, the dot representing the two intervals falls off the 45-degree trend line 19 and, as the difference between successive R-R intervals increases, the dots fall further away from the trend line 19.

The number of dots deviating from the trend line 19 in a Poincare plot can indicate the frequency of occurrence of irregular heartbeats when compared to the number of dots on the trend line 19. The distance of the dots to the trend line 19 can approximate the extent of heart rate change from one heartbeat to the next. However, as heart rate change is limited to only successively-occurring heartbeats, the linearity of time and associated contextual information over an extended time frame are lost. In addition, significant changes in heart rate, particularly spikes in heart rate, such as due to sinus rhythm transitions to atrial flutter, may be masked, distorted or even omitted in a Poincare plot if the change occurs over non-successive heartbeats. In summary, a Poincare plot is more useful as a mathematical tool than a physiological one, and therefore a Poincare plot cannot truly represent what the heart is doing serially over time with respect to changes in the heart's normal and abnormal physiology.

Figure 3:
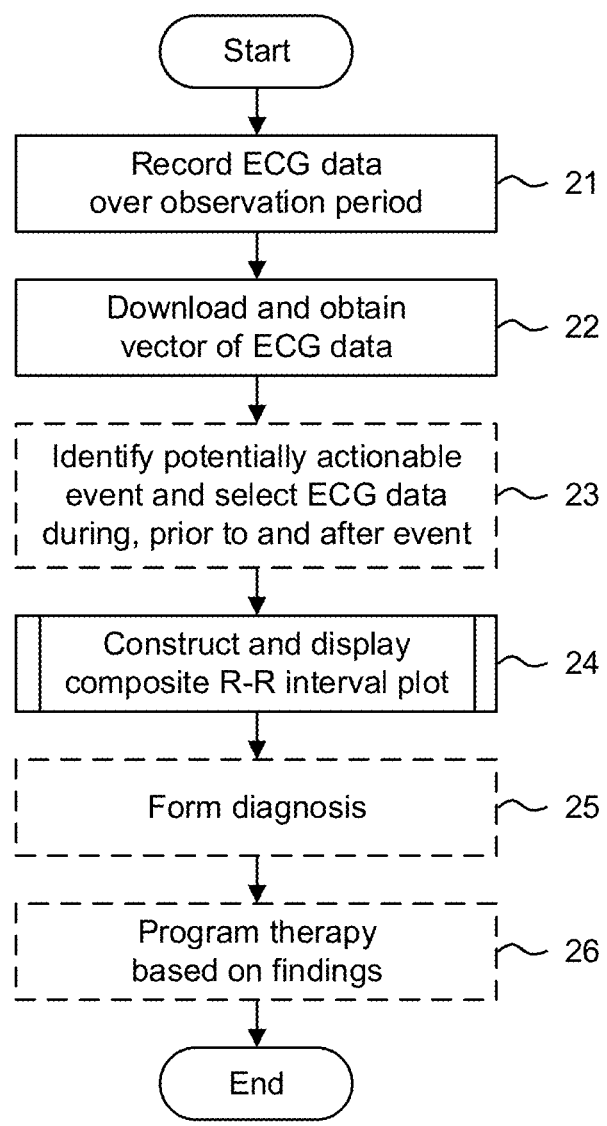
FIG. 3 is a flow diagram showing a method for facilitating diagnosis of cardiac rhythm disorders with the aid of a digital computer in accordance with one embodiment.

Despite the limitations of Poincare plots and related forms of R-R interval tachography, R-R interval data when presented in a format duplicating temporal physiological events remains a key tool that physicians can rely upon to identify temporally-related cardiac dysrhythmic patterns. Interpretation of R-R interval data can be assisted by including multiple temporal points of reference and a plot of R-R interval data that comparatively depicts heart rate variability in concert with R-R interval data. FIG. 3 is a flow diagram showing a method 20 for facilitating diagnosis of cardiac rhythm disorders with the aid of a digital computer in accordance with one embodiment. The method 20 can be implemented in software and execution of the software can be performed on a computer, such as further described infra with reference to FIG. 14, as a series of process or method modules or steps.

As a precursor step, the cutaneous action potentials of a patient are monitored and recorded as ECG data over a set time period (step 21), which can be over a short term or extended time frame. ECG recordation, as well as physiological monitoring, can be provided through various kinds of ECG-capable monitoring ensembles, including a standardized 12-lead ECG setup, such as used for clinical ECG monitoring, a portable Holter-type ECG recorder for traditional ambulatory ECG monitoring, or a wearable ambulatory ECG monitor, such as a flexible extended wear electrode patch and a removable reusable (or single use) monitor recorder, such as described in commonly-assigned U.S. Pat. No. 9,345,414, issued May 24, 2016, the disclosure of which is incorporated by reference, the latter of which includes an electrode patch and monitor recorder that are synergistically optimized to capture electrical signals from the propagation of low amplitude, relatively low frequency content cardiac action potentials, particularly the P-waves, generated during atrial activation. Still other forms of ECG monitoring assembles are possible.

Figure 14:
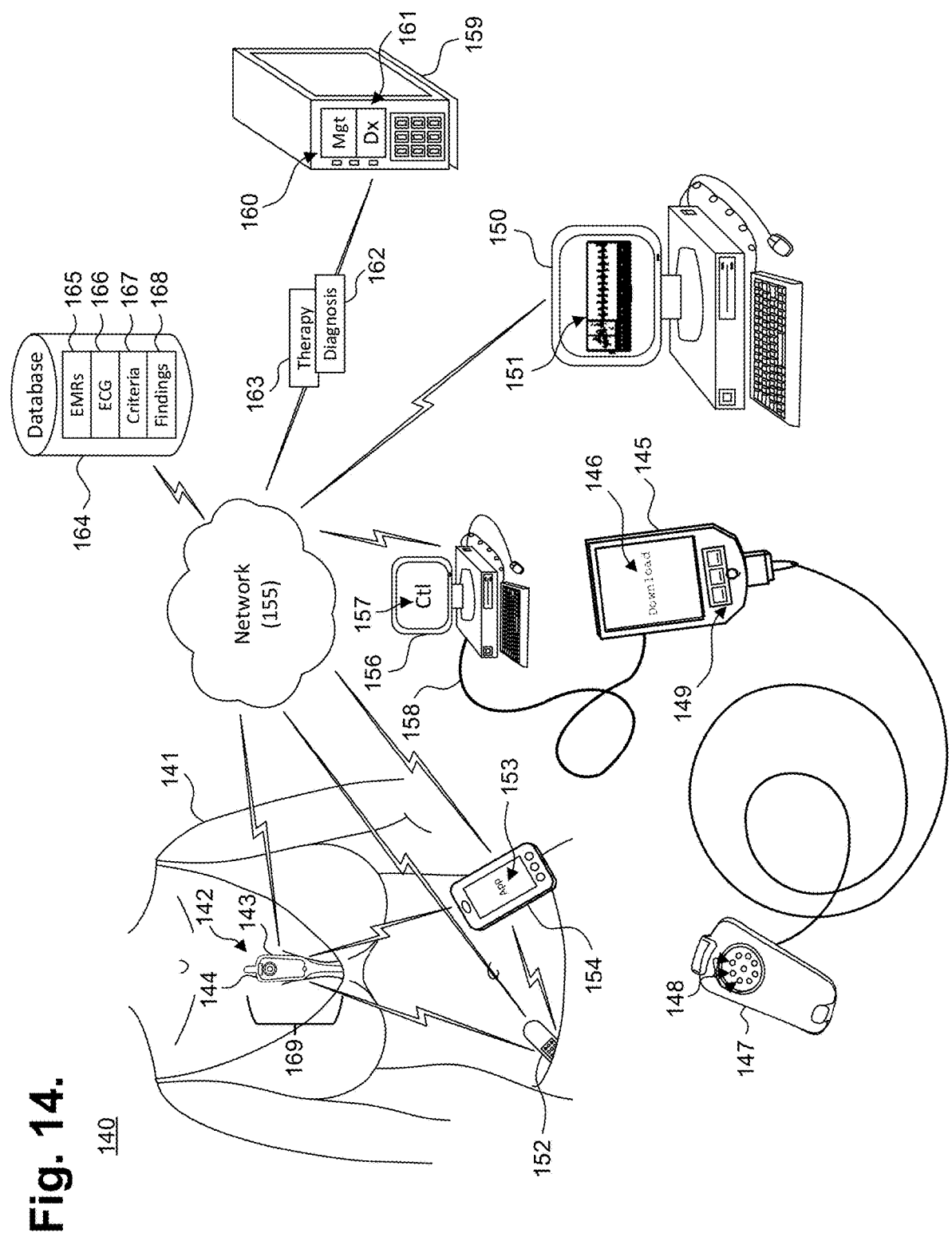
FIG. 14 is a block diagram showing a system for facilitating diagnosis of cardiac rhythm disorders with the aid of a digital computer in accordance with one embodiment.

Upon completion of the monitoring period, the ECG and any physiological data are downloaded or retrieved into a digital computer, as further described infra with reference to FIG. 14, with, for instance, the assistance of a download station or similar device, or via wireless connection, if so equipped, and a vector of the downloaded or retrieved ECG data is obtained (step 22). In one embodiment, the vector of ECG data represents a 40-minute (or other duration) time span that is used in constructing the plot of R-R interval data, although other pre-event and post-event time spans are possible. Optionally, a potentially-actionable cardiac event within the vector of ECG data can be identified and the ECG data during, prior to and after the event is selected (step 23).

The event could be identified with the assistance of a software package, such as Holter LX Analysis Software, licensed by NorthEast Monitoring, Inc., Maynard, Mass.; IntelliSpace Cardiovascular Image and Information management system, licensed Koninklijke Philips N. V., Amsterdam, Netherlands; MoMe System, licensed by InfoBionic, Lowell, Mass.; Pyramis ECG Management, licensed by Mortara Instrument Inc., Milwaukee, Wis.; ICS Clinical Suite, licensed by Spacelabs Healthcare Inc., Snoqualmie, Wash.; or a customized software package. Alternatively, the potentially-actionable cardiac event could be identified by a physician or technician during review of the ECG data.

Figure 4:
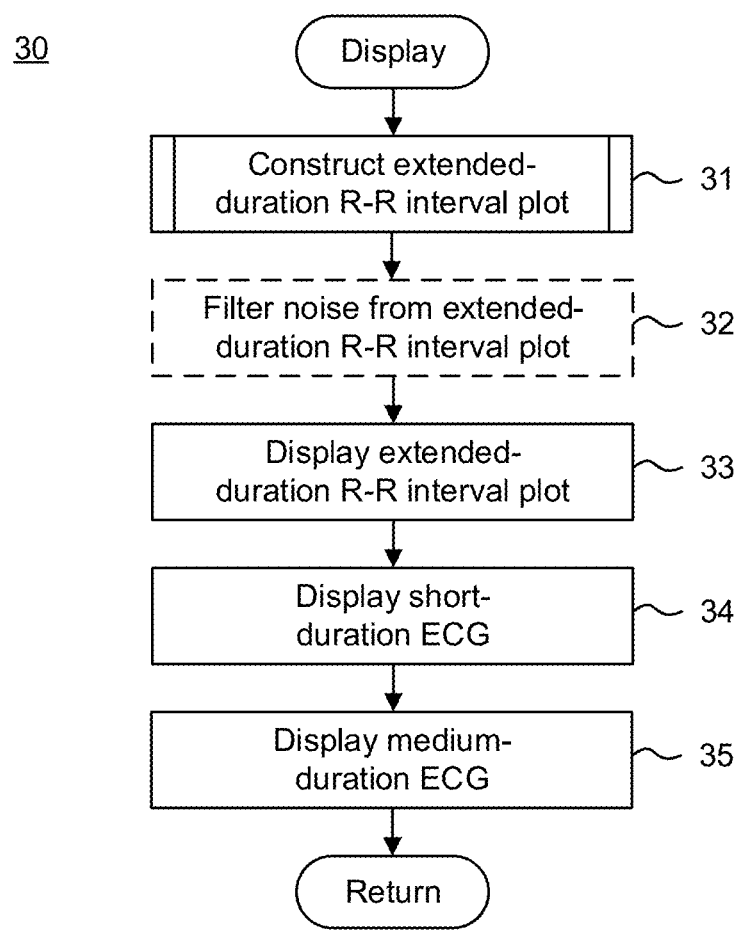
FIG. 4 is a flow diagram showing a routine for constructing and displaying a diagnostic composite plot for use in the method of FIG. 3.

To improve diagnosis of heart rate variability, a diagnostic composite plot is constructed that includes one or more temporal points of reference into the ECG data, which provide important diagnostic context, and a plot of R-R interval data is constructed based on the vector of ECG data (step 24), as further described infra with reference to FIG. 4. Briefly, both near field and far field contextual views of the ECG data are constructed and displayed. Both views are temporally keyed to an extended duration R-R interval data view that, in one embodiment, is scaled non-linearly to maximize the visual differentiation for frequently-occurring heart rate ranges, such that a single glance allows the physician to make a diagnosis. All three views are presented simultaneously, thereby allowing the interpreting physician to diagnose rhythm and the pre- and post-contextual events leading up to a cardiac rhythm of interest.

In a further embodiment, findings made through interpretation of heart rate variability patterns in the diagnostic composite plot can be analyzed to form a diagnosis of a cardiac rhythm disorder (step 25), such as the cardiac rhythm disorders listed, by way of example, in Table 1. For instance, the heart rate variability patterns in the diagnostic composite plot could be provided to a system that programmatically detects AF by virtue of looking for the classic Gaussian-type distribution on the "cloud" of heart rate variability formed in the plot of R-R interval data, which can be corroborated by the accompanying contextual ECG data. Finally, therapy to address diagnosed disorder findings can optionally be programmed into a cardiac rhythm therapy delivery device (step 26), such as an implantable medical device (IMD) (not shown), including a pacemaker, implantable cardioverter defibrillator (ICD), or similar devices.

TABLE 1

Cardiac Rhythm Disorders

Normal sinus rhythm
Sinus Bradycardia
Sinus Tachycardia
Premature atrial and ventricular beats
Ectopic atrial tachycardia
Atrial fibrillation
Atrial flutter
Atrial or ventricular bigeminy, trigeminy or quadrigeminy
Sinus Bradycardia
Fusion beats
Interpolated ventricular premature beats
Cardiac Rhythm Disorders
Intraventricular conduction delay
Junctional rhythm
AV Nodal re-entrant tachycardia
AV re-entrant tachycardia
Wolff-Parkinson-White Syndrome and Pre-excitation
Ventricular tachycardia
Accelerated idioventricular rhythm
AV Wenckebach block
AV Type II block
Sinoatrial block A diagnostic composite plot is constructed and displayed to help physicians identify and diagnose temporally-related cardiac dysrhythmic patterns. The diagnostic composite plot includes ECG traces from two or more temporal points of reference and a plot of R-R interval data, although other configurations of ECG data plots when combined with the R-R interval plot will also provide critical information. FIG. 4 is a flow diagram showing a routine 30 for constructing and displaying a diagnostic composite plot for use in the method 20 of FIG. 3. Specific examples of diagnostic composite plots are discussed in detail infra with reference to FIGS. 7-13.

In the diagnostic composite plot, R-R interval data is presented to physicians in a format that includes views of relevant near field and far field ECG data, which together provide contextual information that improves diagnostic accuracy. In a further embodiment, other views of ECG data can be provided in addition to or in lieu of the near field and far field ECG data views. The near field (or short duration) ECG data provides a "pinpoint" classical view of an ECG at traditional recording speed in a manner that is known to and widely embraced by physicians. The near field ECG data is coupled to a far field (or medium duration) ECG data view that provides an "intermediate" lower resolution, pre- and post-event contextual view. Thus, the extended-duration R-R interval plot is first constructed (step 31), as further described infra with reference to FIG. 5. Optionally, noise can be filtered from the R-R interval plot (step 32), which is then displayed (step 33). Noise filtering can include lowpass or high-pass filtering or other forms of signal processing, including automatic gain control, such as described in commonly-assigned U.S. Pat. No. 9,345,414, cited supra.

Rhythm disorders have different weightings depending upon the context with which they occur. In the diagnostic composite plot, the R-R interval data view and the multiple views of the ECG data provide that necessary context. Effectively, the short and medium duration ECG data that accompanies the extended-duration R-R interval plot represents the ECG data "zoomed" in around a temporal point of reference identified in the center (or other location) of the R-R interval plot, thereby providing a visual context to the physician that allows temporal assessment of cardiac rhythm changes in various complementary views of the heart's behavior. The durations of the classical "pinpoint" view, the pre- and post-event "intermediate" view, and the R-R interval plot are flexible and adjustable. In one embodiment, the diagnostic composite plot displays R-R interval data over a forty-minute duration and ECG data over short and medium durations (steps 34 and 35), such as four-second and 24-second durations that provide two- and 12-second segments of the ECG data before and after the R-R interval plot's temporal point of reference, which is generally in the center of the R-R interval plot, although other locations in the R-R interval plot could be identified as the temporal point of reference. The pinpoint "snapshot" and intermediate views of ECG data with the extended term R-R interval data comparatively depicts heart rate context and patterns of behavior prior to and after a clinically meaningful arrhythmia or patient concern, thereby enhancing diagnostic specificity of cardiac rhythm disorders and providing physiological context to improve diagnostic ability. In a further embodiment, diagnostically relevant cardiac events can be identified and the R-R interval plot can be constructed with a cardiac event centered in the middle (or other location) of the plot, which thereby allows pre- and post-event heart rhythm data to be contextually "framed" through the pinpoint and intermediate ECG data views. Other durations, intervals and presentations of ECG data are possible.

Figure 5:
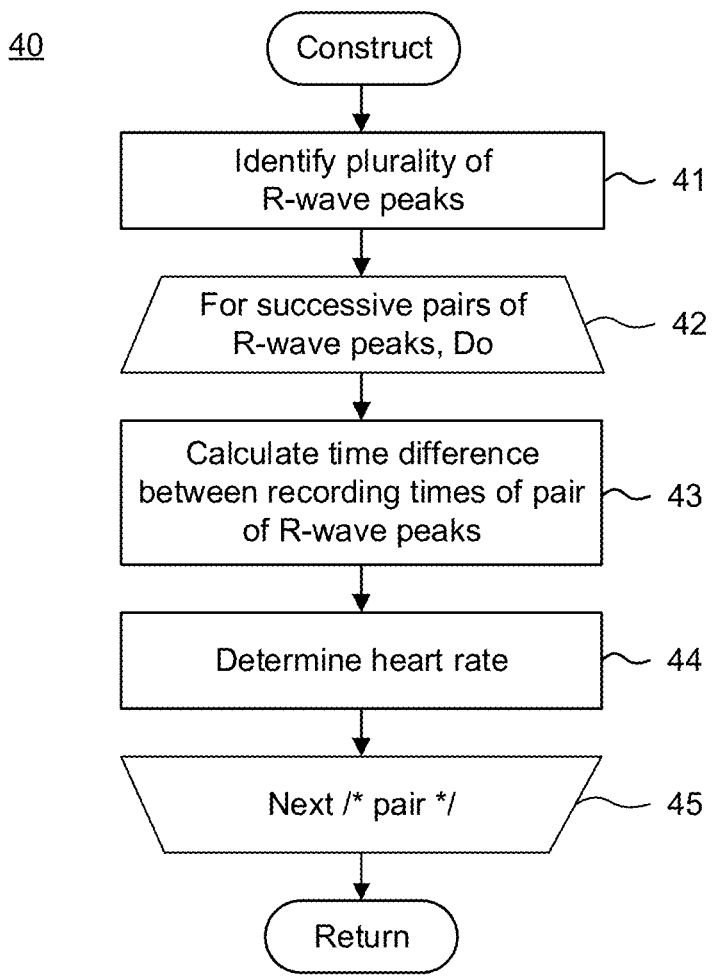
FIG. 5 is a flow diagram showing a routine for constructing an extended-duration R-R interval plot for use in the routine of FIG. 4.

The extended-duration R-R interval plot presents beat-to-beat heart rate variability in a format that is intuitive and contextual, yet condensed. The format of the R-R interval plot is selected to optimize visualization of cardiac events in a compressed, yet understandable field of view that allows for compact presentation of the data akin to a cardiologist's understanding of clinical events. FIG. 5 is a flow diagram showing a routine 40 for constructing an extended-duration R-R interval plot for use in the routine 30 of FIG. 4. The duration of the R-R interval plot can vary from less than one minute to the entire duration of the recording. Thus, a plurality of R-wave peaks is first selected out of the vector of ECG data (step 41) appropriate to the duration of the R-R interval plot to be constructed. For successive pairs of the R-wave peaks (steps 42-43), the difference between the recording times of the R-peaks is calculated (step 43). Each recording time difference represents the length of one heartbeat. The heart rate associated with the recording time difference is determined by taking an inverse of the recording time difference and normalizing the inverse to beats per minute (step 44). Taking the inverse of the recording time difference yields a heart rate expressed in beats per second, which can be adjusted by a factor of 60 to provide a heart rate expressed in bpm. Calculation of the differences between the recording times and the associated heart rate continues for all of the remaining pairs of the R-wave peaks (step 44).

The pairings of R-R intervals and associated heart rates are formed into a two-dimensional plot. R-R intervals are plotted along the x-axis and associated heart rates are plotted along the y-axis. The range and scale of the y-axis (heart rate) can be adjusted according to the range and frequency of normal or patient-specific heart rates, so as to increase the visual distinctions between the heart rates that correspond to different R-R intervals. In one embodiment, the y-axis of the R-R interval plot has a range of 20 to 300 beats per minute and R-R intervals corresponding to heart rates falling extremely outside of this range are excluded to allow easy visualization of 99+% of the heart rate possibilities.

In a further embodiment, the y-axis has a non-linear scale that is calculated as a function of the x-axis (R-R interval), such that:

$$y = \left(\frac{x - \min \text{bpm}}{\max \text{bpm} - \min \text{bpm}}\right)^n$$

where x is the time difference, min bpm is the minimum heart rate, max bpm is the maximum heart rate, and n<1. The non-linear scale of the y-axis accentuates the spatial distance between successive heart rates when heart rate is low. For example, when n=2, the spatial difference between 50 and 60 bpm is 32% larger than the spatial difference between 90 bpm and 100 bpm, and 68% larger than the spatial difference between 150 bpm and 160 bpm. As a result the overall effect is to accentuate the spatial differences in frequently-occurring ranges of heart rate and de-emphasize the spatial differential in ranges of heart rate where a deviation from norm would have been apparent, thus maximizing the spatial efficiency in data presentation. The goal is to show cardiac events in a simple, small visual contextual format. Larger scales and larger formats belie the practical limits of single-page presentations for the easy visualization at a glance by the busy physician. The visual distinctions between the heart rates that correspond to different R-R intervals stand out, especially when plotted on a non-linear scale. Other y-axis ranges and scales are possible as may be selected by distinct clinical needs and specific diagnostic requirements.

Figure 6:
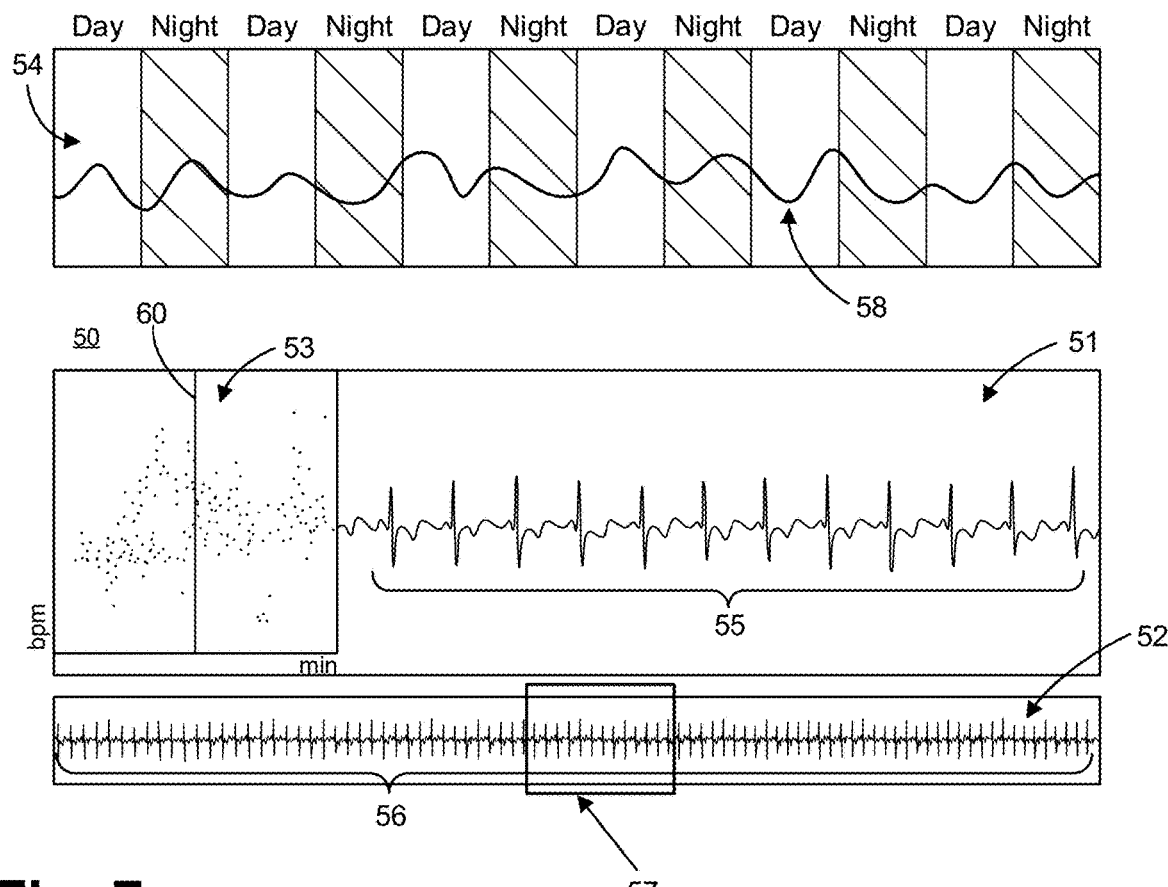
FIG. 6 is a diagram showing, by way of example, a diagnostic composite plot generated by the method of FIG. 3.

The diagnostic composite plot includes a single, long range view of R-R interval data and a pair of pinpoint ECG data views that together help to facilitate rhythm disorder diagnosis by placing focused long-term heart rate information alongside short-term and medium-term ECG information. Such pairing of ECG and R-R interval data is unique in its ability to inform the physician of events prior to, during and after a cardiovascular event. FIG. 6 is a diagram showing, by way of example, a diagnostic composite plot 50 generated by the method 30 of FIG. 3. Note that the diagnostic composite plot can be tailored to include more than one view of R-R interval data and as many views of contextual ECG data as needed. In a further embodiment, a background information plot presenting an extended far field of related information can be included, such as activity amount, activity intensity, posture, syncope impulse detection, respiratory rate, blood pressure, oxygen saturation ($SpO_2$), blood carbon dioxide level ($pCO_2$), glucose, lung wetness, and temperature. Other forms of background information are possible. In a still further embodiment, background information can be layered on top of or keyed to the diagnostic composite plot 50, particularly at key points of time in the R-R interval data plot, so that the context provided by each item of background information can be readily accessed by the reviewing physician.

The diagnostic composite plot 50 includes an ECG plot presenting a near field (short duration) view 51, an ECG plot presenting an intermediate field (medium duration) view 52, and an R-R interval data plot presenting a far field (extended duration) view 53. The three views 51, 52, 53 are juxtaposed alongside one other to allow quick back and forth referencing of the full context of the heart's normal and abnormal physiology. Typically, a temporal point of reference, which could be a diagnostically relevant cardiac event, patient concern or other indicia, would be identified and centered on the x-axis in all three views. The placement of the temporal point of reference in the middle of all three x-axes enables the ECG data to be temporally keyed to the R-R interval data appearing in the center 60 of the R-R interval data view 53, with a near field view 51 of an ECG displayed at normal (paper-based) recording speed and a far field view 52 that presents the ECG data occurring before and after the center 60. As a result, the near field view 51 provides the ECG data corresponding to the R-R interval data at the center 60 (or other location) in a format that is familiar to all physicians, while the intermediate field view 52 enables presentation of the broader ECG data context going beyond the borders of the near field view 51. In a further embodiment, the center 60 can be slidably adjusted backwards and forwards in time, with the near field view 51 and the far field view 52 of the ECG data automatically adjusting accordingly to stay in context with the R-R interval data view 51. In a still further embodiment, multiple temporal points of reference can be identified with each temporal point of reference being optionally accompanied by one or more dedicated sets of ECG data views.

The collection of plots are conveniently arranged close enough to one another to facilitate printing on a single page of standard sized paper (or physical paper substitute, such as a PDF file), although other layouts of the plots are possible. The far field view 53 is plotted with time in the x-axis and heart rate in the y-axis. The R-R intervals are calculated by measuring the time occurring between successive R-wave peaks. In one embodiment, the far field view 53 presents R-R interval data (expressed as heart rate in bpm) that begins about 20 minutes prior to and ends about 20 minutes following the center 60, although other durations are possible.

The near field view 51 and intermediate field view 52 present ECG data relative to the center 60 of the far field view 53. The near field view 51 provides a pinpoint or short duration view of the ECG data. In one embodiment, the near field view 51 presents ECG data 55 that begins about two seconds prior to and ends about two seconds following the center 60, although other durations are possible. The intermediate field view 52 provides additional contextual ECG information allowing the physician to assess the ECG itself and gather a broader view of the rhythm before and after a "blow-up" of the specific arrhythmia of interest. In one embodiment, the intermediate field view 52 presents ECG data 56 that begins about 12 seconds prior to and ends about 12 seconds following the center 60, although other durations are possible. For convenience, the eight-second interval of the ECG data 56 in the intermediate field view 52 that makes up the ECG data 56 in the near field view 51 is visually highlighted, here, with a surrounding box 57. In addition, other views of the ECG data, either in addition to or in lieu of the near field view 51 and the far field view 52 are possible. Optionally, an ECG plot presenting an extended far field view 54 of the background information can be included in the diagnostic composite plot 50. In one embodiment, the background information is presented as average heart rate with day and night periods 58 alternately shaded along the x-axis. Other types of background information, such as activity amount, activity intensity, posture, syncope impulse detection, respiratory rate, blood pressure, oxygen saturation ($SpO_2$), blood carbon dioxide level ($pCO_2$), glucose, lung wetness, and temperature, are possible.

Figure 7:
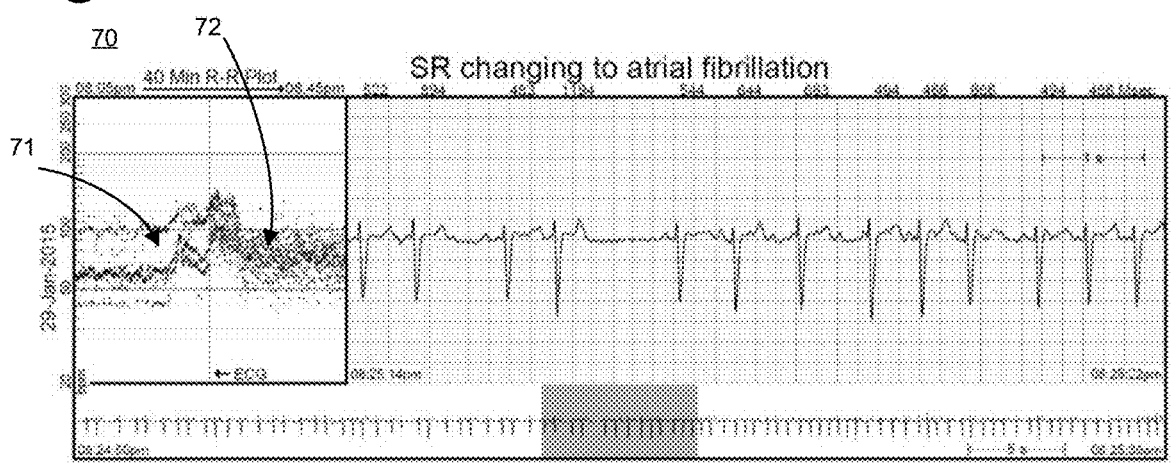
FIG. 7 is a diagram showing, by way of example, a diagnostic composite plot for facilitating the diagnosis of sinus rhythm (SR) transitioning into atrial fibrillation (AF).

Examples of the diagnostic composite plot as applied to specific forms of cardiac rhythm disorders will now be discussed. These examples help to illustrate the distinctive weightings that accompany different forms of rhythm disorders and the R-R interval and ECG waveform deflection context with which they occur. FIG. 7 is a diagram showing, by way of example, a diagnostic composite plot 70 for facilitating the diagnosis of sinus rhythm (SR) transitioning into AF. SR is indicated through the presence of a reasonably steady baseline, but with subsidiary lines of premature beats and their compensatory pauses. SR manifests as a shadowing 71 of a high heart rate line and a low heart rate line. AF is characterized by irregular heartbeats with a somewhat random variation of R-R intervals, although within a limited range and concentrating in a Gaussian-like distribution pattern around a mean that varies over time. Although AF can be diagnosed by viewing a near field view 51 of ECG data showing heartbeats with reversed P-wave and irregular R-R intervals, this approach may be unclear when viewing "snippets" of ECG data, especially when associated with poor quality ECG signals. The presence of AF can also be confirmed through a far field view 53 of R-R interval data, in which the R-R intervals assume superficially appearing disorganized, spread-out and decentralized scattered cloud 72 along the x-axis, in comparison to a concentrated, darkened line typical of a more organized cardiac rhythm.

Figure 8:
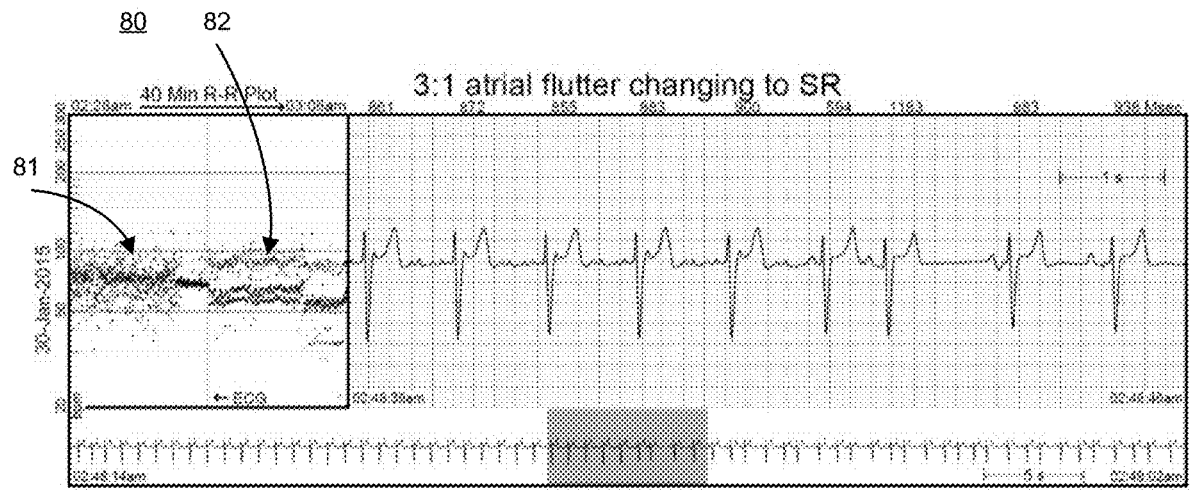
FIG. 8 is a diagram showing, by way of example, a diagnostic composite plot for facilitating the diagnosis of 3:1 atrial flutter (AFL) transitioning into SR.

FIG. 8 is a diagram showing, by way of example, a diagnostic composite plot 80 for facilitating the diagnosis of 3:1 atrial flutter (AFL) transitioning into SR with frequent premature ectopic atrial beats. In the initial part of the R-R interval plot, the R-R intervals have a discernible aggregated line in the middle of the cloud 81 when the rhythm has yet to stabilize into a set pattern, not quite AF and not quite AFL. Immediately thereafter, a dense line representing firm 3:1 atrial flutter stabilizes the rhythm prior to the transition into SR associated with the presence of two seesawing baselines that result from frequent atrial ectopy causing short coupling intervals and then compensatory long coupling intervals. SR is indicated by the middle of the three lines with a low heart rate line consistent with the compensatory pause (long coupling interval) and a high heart rate line with the shortest coupling interval representing the series of atrial premature beats 82, and thus, at a faster heart rate.

Figure 9:
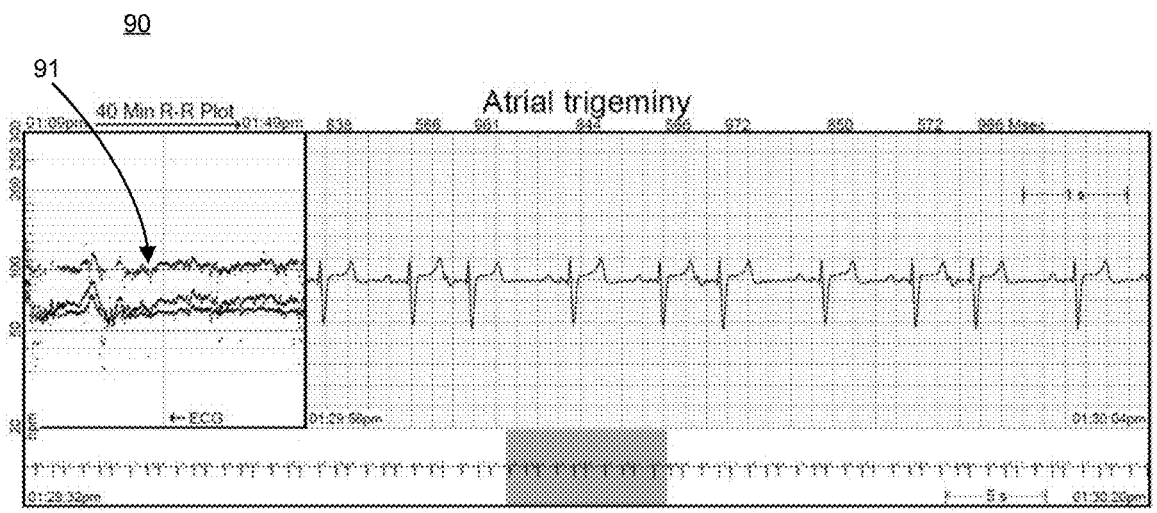
FIG. 9 is a diagram showing, by way of example, a diagnostic composite plot for facilitating the diagnosis of atrial trigeminy.

FIG. 9 is a diagram showing, by way of example, a diagnostic composite plot 90 for facilitating the diagnosis of atrial trigeminy. Atrial trigeminy is characterized by three heartbeat rates appearing intermittently yet reasonably regularly. Although atrial trigeminy can be diagnosed by viewing a near field view 51 of ECG data, the pattern is significantly more recognizable in a far field view 53 of R-R interval data, in which a repeating pattern of three distinct heartbeat lines are persistently present and clearly visible 91. This view also provides the physician with a qualitative feel for the frequency of the event troubling the patient that is not discernible from a single ECG strip.

Figure 10:
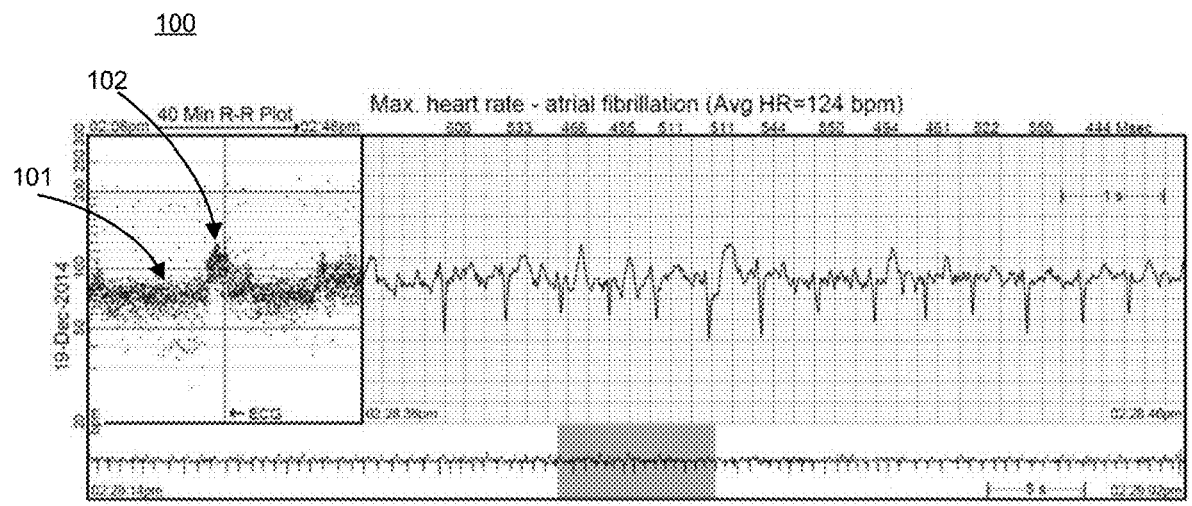
FIG. 10 is a diagram showing, by way of example, a diagnostic composite plot for facilitating the diagnosis of maximum heart rate in an episode of AF during exercise.

FIG. 10 is a diagram showing, by way of example, a diagnostic composite plot 100 for facilitating the diagnosis of maximum heart rate in an episode of AF during exercise. In a far field view 50 of R-R interval data, AF manifests through a dispersed cloud of dots (Gaussian-like distribution) without a discernible main heart rate line representing regular heartbeats 101. Under exercise, the maximum heartbeat can be located by an increase in heart rate clustered about the cloud 102. In addition, individual dots above the 200 bpm range throughout the entire 40-minute range indicates the maximum heart rate during exercise. The very rapid rise in heart rate can be critical to patient management, as such bumps in rate by exercise can prove serious and even trigger cardiac arrest. Their very presence is easily visualized in the R-R interval data plot, thereby allowing the physician to alter therapy sufficiently to control such potentially damaging rises in heart rate.

Figure 11:
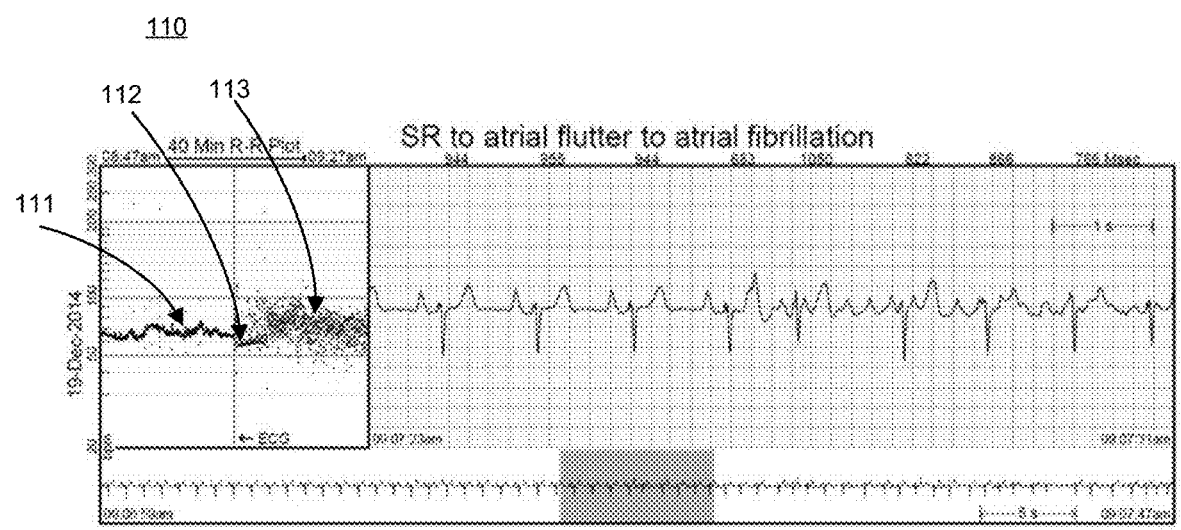
FIG. 11 is a diagram showing, by way of example, a diagnostic composite plot for facilitating the diagnosis of SR transitioning into AFL transitioning into AF.

FIG. 11 is a diagram showing, by way of example, a diagnostic composite plot 110 for facilitating the diagnosis of SR transitioning into AFL transitioning into AF. In a far field view 53 of R-R interval data, SR manifests as an uneven main heart rate line with a fluctuating height 111. At the onset of AFL, the main heart rate line breaks away at a lower heart rate than the SR main heart rate line 112. The episode of AFL further evolves into AF as characterized by a dispersed cloud of irregular heartbeats without concentrated heart rate lines 113. This view provides critical information to the physician managing AF patients in that, at a glance, the view provides data that tells the physician that the patient's AF may be the consequence of AFL. Such knowledge may alter both drug and procedure therapies, like catheter ablation details of intervention.

Figure 12:
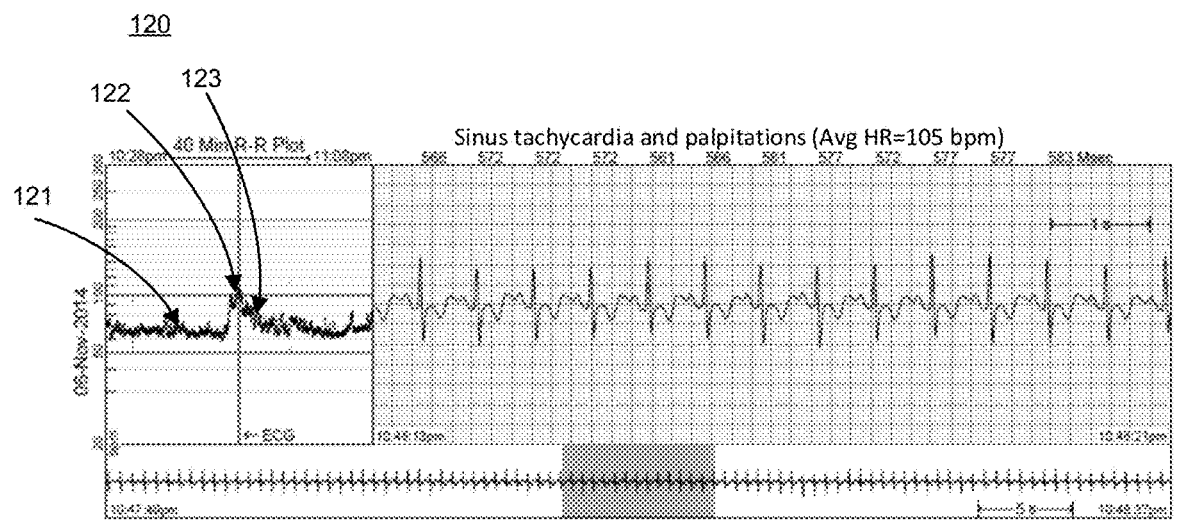
FIG. 12 is a diagram showing, by way of example, a diagnostic composite plot for facilitating the diagnosis of sinus tachycardia and palpitations that occurred during exercise accompanied by a jump in heart rate.

FIG. 12 is a diagram showing, by way of example, a diagnostic composite plot 120 for facilitating the diagnosis of sinus tachycardia and palpitations that occurred during exercise accompanied by a jump in heart rate. In a far field view 50 of R-R interval data, sinus tachycardia is indicated by the presence of a baseline heart rate of about 60 bpm 121 that spikes up to around 100 bpm 122 and gradually slopes down with a wide tail 123, reflecting a sharp rise of heart rates followed by a gradual decline. The associated ECG data in the near field and intermediate field views (not shown) can confirm the rhythm as sinus rhythm and a normal response to exercise. This rhythm, although superficially obvious, was associated with symptoms of palpitations and demonstrates a sensitivity to heart rate fluctuations, rather than a sensitivity to an arrhythmia. This common problem is often dismissed as merely sinus tachycardia, rather than recognizing the context of a changing rate that generated the patient's complaint, a problem, visible only in the R-R interval data plot.

Figure 13:
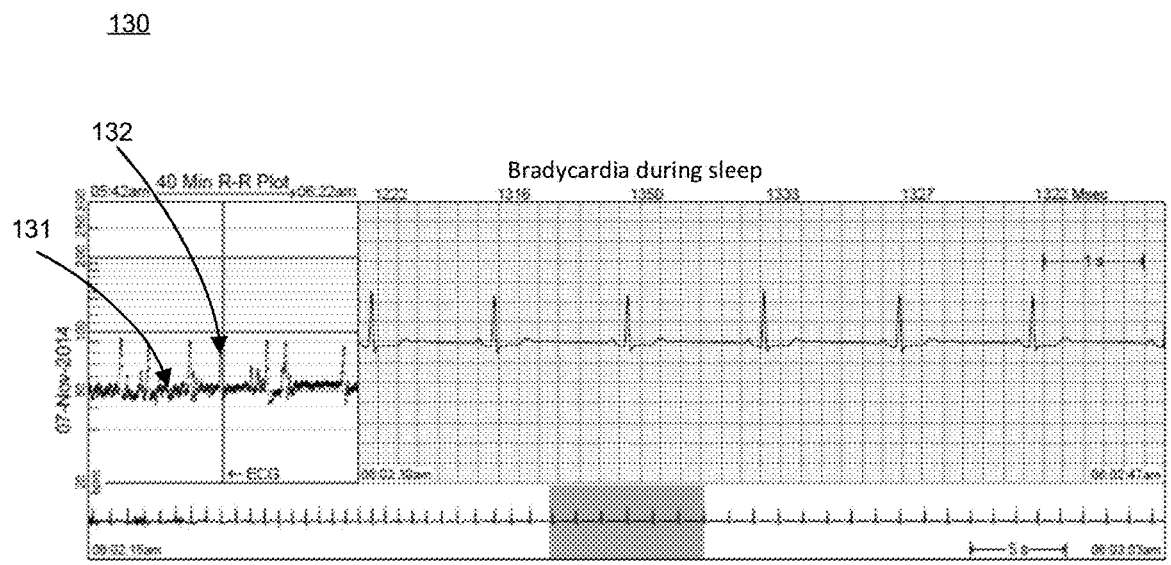
FIG. 13 is a diagram showing, by way of example, a diagnostic composite plot for facilitating the diagnosis of bradycardia.

FIG. 13 is a diagram showing, by way of example, a diagnostic composite plot 90 for facilitating the diagnosis of bradycardia during sleep and a R-R interval pattern characteristic of sleep. Bradycardia refers to a resting heart rate of under 60 bpm. Bradycardia during sleep is often tempered with occasional spikes of rapid heart rate, which can be a secondary compensatory response to dreaming, snoring or sleep apnea. In a far field view 50 of R-R interval data, bradycardia manifests as the presence of a base line heart rate in the range of about 50 bpm 131, coupled with multiple spikes of dots 132 representing intermittent episodes of elevated heart rate. Such elevations in heart rate during a pre-dominantly slower rate may be signs of a cardio-respiratory disorder. Still other applications of the diagnostic composite plot 80 are possible.

The diagnostic composite plots are a tool used by physicians as part of a continuum of cardiac care provisioning that begins with ECG monitoring, continues through diagnostic overread and finally, if medically appropriate, concludes with cardiac rhythm disorder treatment. Each of these steps involve different physical components that collaboratively allow physicians to acquire and visualize R-R interval and ECG data in a way that accurately depicts heart rate variability over time. FIG. 14 is a block diagram showing a system 140 for facilitating diagnosis of cardiac rhythm disorders with the aid of a digital computer 150 in accordance with one embodiment. Each diagnostic composite plot 151 is based on ECG data 166 that has either been recorded by a conventional electrocardiograph (not shown) or retrieved or obtained from some other type of ECG monitoring and recording device. Following completion of the ECG monitoring, the ECG data is assembled into a diagnostic composite plot 151, which can be used by a physician to diagnosis and, if required, treat a cardiac rhythm disorder, or for other health care or related purposes.

Each diagnostic composite plot 151 is based on ECG data 166 that has been recorded over a period of observation, which can be for just a short term, such as during a clinic appointment, or over an extended time frame of months. ECG recordation and, in some cases, physiological monitoring can be provided through various types of ECG-capable monitoring ensembles, including a standardized 12-lead ECG setup (not shown), such as used for clinical ECG monitoring, a portable Holter-type ECG recorder for traditional ambulatory ECG monitoring (also not shown), or a wearable ambulatory ECG monitor.

One form of ambulatory ECG monitor 142 particularly suited to monitoring and recording ECG and physiological data employs an electrode patch 143 and a removable reusable (or single use) monitor recorder 144, such as described in commonly-assigned U.S. Pat. No. 9,345,414, cited supra. The electrode patch 143 and monitor recorder 144 are synergistically optimized to capture electrical signals from the propagation of low amplitude, relatively low frequency content cardiac action potentials, particularly the P-waves generated during atrial activation. The ECG monitor 142 sits centrally (in the midline) on the patient's chest along the sternum 169 oriented top-to-bottom. The ECG monitor 142 interfaces to a pair of cutaneous electrodes (not shown) on the electrode patch 143 that are adhered to the patient's skin along the sternal midline (or immediately to either side of the sternum 169). The ECG monitor 142 has a unique narrow "hourglass"-like shape that significantly improves the ability of the monitor to be comfortably worn by the patient 141 for an extended period of time and to cutaneously sense cardiac electric signals, particularly the P-wave (or atrial activity) and, to a lesser extent, the QRS interval signals in the ECG waveforms indicating ventricular activity.

The electrode patch 143 itself is shaped to conform to the contours of the patient's chest approximately centered on the sternal midline. To counter the dislodgment due to compressional and torsional forces, a layer of non-irritating adhesive, such as hydrocolloid, is provided at least partially on the underside, or contact, surface of the electrode patch, but only on the electrode patch's distal and proximal ends. To counter dislodgment due to tensile and torsional forces, a strain relief is defined in the electrode patch's flexible circuit using cutouts partially extending transversely from each opposite side of the flexible circuit and continuing longitudinally towards each other to define in 'S'-shaped pattern. In a further embodiment, the electrode patch 143 is made from a type of stretchable spunlace fabric. To counter patient bending motions and prevent disadhesion of the electrode patch 143, the outward-facing aspect of the backing, to which a (non-stretchable) flexible circuit is fixedly attached, stretches at a different rate than the backing's skin-facing aspect, where a skin adhesive removably affixes the electrode patch 143 to the skin. Each of these components are distinctive and allow for comfortable and extended wear, especially by women, where breast mobility would otherwise interfere with ECG monitor use and comfort. Still other forms of ECG monitoring and recording assembles are possible.

When operated standalone, the monitor recorder 142 senses and records the patient's ECG data 166 and physiological data (not shown) into a memory onboard the monitor recorder 144. The recorded data can be downloaded using a download station 147, which could be a dedicated download station 145 that permits the retrieval of stored ECG data 166 and physiological data, if applicable, execution of diagnostics on or programming of the monitor recorder 144, or performance of other functions. To facilitate physical connection with the download station 145, the monitor recorder 144 has a set of electrical contacts (not shown) that enable the monitor recorder 144 to physically interface to a set of terminals 148. In turn, the download station 145 can be operated through user controls 149 to execute a communications or data download program 146 ("Download") or similar program that interacts with the monitor recorder 144 via the physical interface to retrieve the stored ECG data 166. The download station 145 could alternatively be a server, personal computer, tablet or handheld computer, smart mobile device, or purpose-built device designed specific to the task of interfacing with a monitor recorder 144. Still other forms of download station 145 are possible. In a further embodiment, the ECG data 166 from the monitor recorder 144 can be offloaded wirelessly.

The ECG data 166 can be retrieved from the download station 145 using a control program 157 ("Ctl") or analogous application executing on a personal digital computer 156 or other connectable computing device, via a hard wired link 158, wireless link (not shown), or by physical transfer of storage media (not shown). The personal digital computer 156 may also execute middleware (not shown) that converts the ECG data 166 into a format suitable for use by a third-party post-monitoring analysis program. The personal digital computer 156 stores the ECG data 166 along with each patient's electronic medical records (EMRs) 165 in the secure database 64, as further discussed infra. In a further embodiment, the download station 145 is able to directly interface with other devices over a computer communications network 155, which could be a combination of local area and wide area networks, including the Internet or another telecommunications network, over wired or wireless connections.

A client-server model can be employed for ECG data 166 analysis. In this model, a server 62 executes a patient management program 160 ("Mgt") or similar application that accesses the retrieved ECG data 166 and other information in the secure database 164 cataloged with each patient's EMRs 165. The patients' EMRs can be supplemented with other information (not shown), such as medical history, testing results, and so forth, which can be factored into automated diagnosis and treatment. The patient management program 160, or other trusted application, also maintains and safeguards the secure database 164 to limit access to patient EMRs 165 to only authorized parties for appropriate medical or other uses, such as mandated by state or federal law, such as under the Health Insurance Portability and Accountability Act (HIPAA) or per the European Union's Data Protection Directive. Other schemes and safeguards to protect and maintain the integrity of patient EMRs 165 are possible.

In a further embodiment, the wearable monitor 142 can interoperate wirelessly with other wearable or implantable physiology monitors and activity sensors 152, such as activity trackers worn on the wrist or body, and with mobile devices 153, including smart watches and smartphones. Wearable or implantable physiology monitors and activity sensors 152 encompass a wide range of wirelessly interconnectable devices that measure or monitor a patient's physiological data, such as heart rate, temperature, blood pressure, respiratory rate, blood pressure, blood sugar (with or without an appropriate subcutaneous probe), oxygen saturation, minute ventilation, and so on; physical states, such as movement, sleep, footsteps, and the like; and performance, including calories burned or estimated blood glucose level. Frequently, wearable and implantable physiology monitors and activity sensors 152 are capable of wirelessly interfacing with mobile devices 153, particularly smart mobile devices, including so-called "smartphones" and "smart watches," as well as with personal computers and tablet or handheld computers, to download monitoring data either in real-time or in batches through an application ("App") or similar program.

Based on the ECG data 166, physicians can rely on the data as medically certifiable and are able to directly proceed with diagnosing cardiac rhythm disorders and determining the appropriate course of treatment for the patient 141, including undertaking further medical interventions as appropriate. The ECG data 166 can be retrieved by a digital computer 150 over the network 155. A diagnostic composite plot 151 that includes multiple temporal points of reference and a plot of R-R interval data is then constructed based on the ECG data 166, as discussed in detail supra with reference to FIG. 3, and displayed or, alternatively, printed, for use by a physician.

In a further embodiment, the server 159 executes a patient diagnosis program 161 ("Dx") or similar application that can evaluate the ECG data 166 to form a diagnosis of a cardiac rhythm disorder. The patient diagnosis program 161 compares and evaluates the ECG data 166 to a set of medical diagnostic criteria 167, from which a diagnostic overread 162 ("diagnosis") is generated. Each diagnostic overread 162 can include one or more diagnostic findings 168 that can be rated by degree of severity, such as with the automated diagnosis of atrial fibrillation. If at least one of the diagnostic findings 168 for a patient exceed a threshold level of tolerance, which may be tailored to a specific client, disease or medical condition group, or applied to a general patient population, in a still further embodiment, therapeutic treatment ("Therapy") to address diagnosed disorder findings can be generated and, optionally, programmed into a cardiac rhythm therapy delivery device, such as an IMD (not shown), including a pacemaker, implantable cardioverter defibrillator (ICD), or similar devices. Diagnosis of cardiac rhythm disorders can also be facilitated via transformed displays of the cardiac data and an interactive user interface through which the data displays can be manipulated. As technology improves with respect to medical devices and larger amounts of data are able to be collected during a single recording, such as over a period of 7-14 days or longer, displaying the data can become problematic since displays are limited to a size of the screen or monitor on which the data is displayed. As the amount of data increases, the ability to display all the data at a single time becomes more difficult. Further, displaying all the data at a single time provides a broad view of the general cardiac rhythm, but not the finer details, such as the individual waves. Accordingly, most cardiac data is provided in finer detail to assist a medical professional in diagnosis; however, the broad or full view can also be extremely helpful to a diagnosing professional. For instance, in the broad view, some types of rhythm disorders can be identified easier than in a detailed view.

Figure 15:
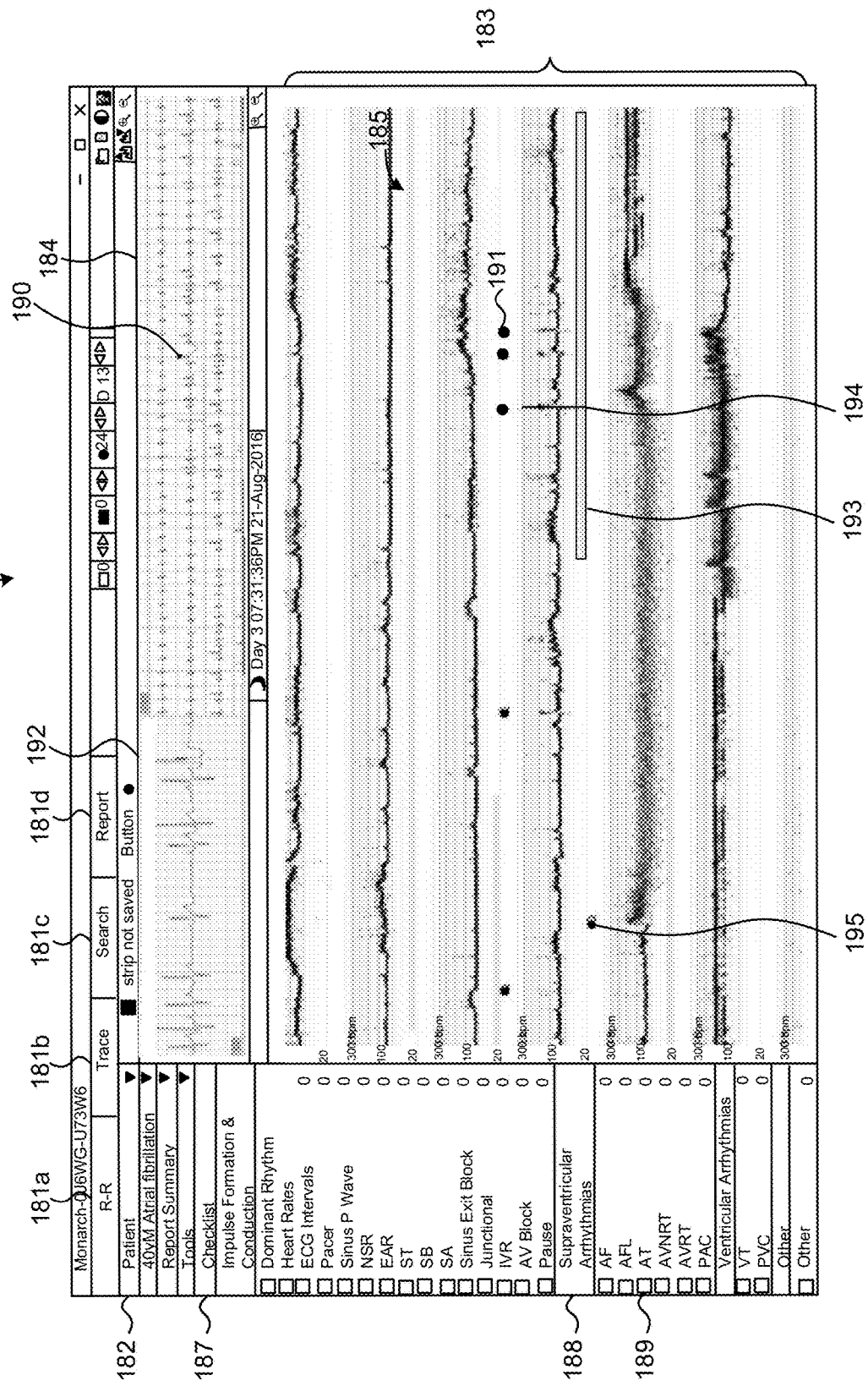
FIG. 15 is a screenshot of an interactive user interface for displaying an overview of an R-R plot.

Accordingly, the ability to provide a broad or full view, while allowing a user to zoom in and out of the view, in a sliding fashion, permits the user to view finer details of the broad view sequentially. Further, allowing marking of the cardiac data, such as identifying and designating portions of the cardiac data with an event, provide an overview of a patient's cardiac health. Such transformed data displays and interactive user interface can be used to select or identify sections of cardiac data for including in the diagnostic composite plot. FIG. 15 is a screenshot of an interactive user interface 180 for displaying an overview of an R-R plot. The user interface can be presented via a web page or software application. For example, a web page 180 can include tabs 181a-d provided at a top of the web page 180 for directing to other web pages associated with those tabs. The tabs can include tabs for R-R overview 181a, ECG Trace overview 181b, Search 181c, and Report 181d. The web pages associated with each of the Trace 181b, Search 181c, and Report 181d tabs are discussed below in detail with respect to FIGS. 21, 26, and 27.

The web page 180 associated with the R-R overview tab 181a can provide a patient summary bar 182, an R-R plot 183, a mid-length ECG trace plot 184, and a short-length ECG trace plot 192. However, other types of data can be provided on the web page 180. The patient summary bar 182 can include a summary of the patient data including name, birthdate, physician, and age, as well as other types of patient information, a checklist 187 of different types of cardiac events 189, which can be categorized, into groups, such as superventricular arrhythmia and ventricular arrhythmia, as further discussed below with respect to FIG. 18.

The overview R-R plot data, which can be constructed as described above with respect to FIG. 5, can be displayed over a predetermined amount of time or for the recording lifespan of a monitor that obtains the ECG data for the R-R plot. In one embodiment, a wearable ambulatory ECG monitor, as described above with respect to FIG. 14, can record ECG data over a period of days, such as seven or more days. However, other recording times and recording devices are possible.

The mid-length ECG trace 184 and short-length ECG trace 192 can each include a portion of the ECG data that corresponds with a designated point 194 on the R-R overview. The designated point can be indicated via a marker 194, such as a line or other type of marker. Each of the mid-length ECG trace 184 and the short-length ECG trace 192 include a predetermined amount of ECG data prior to and after the point designated by the marker 194, with the mid-length ECG trace including ECG data over a longer time period than the short-length ECG trace. Any actions performed within the relevant portions of the R-R overview can be reflected in the short-length and mid-length views of the ECG trace. For example, if a user clicks on a location within the R-R overview, the short- and mid-length views can change accordingly. Otherwise, if a marker is placed within the R-R overview, the marker can also be placed within one or both of the short- and mid-length traces.

The R-R plot data 183 can be linearly arranged along rows beginning on a left side of the web page to a right side and then continuing left to right on a further row located below the previous row. Each row can be numbered sequentially with the first row representing the earliest recorded cardiac data and the last row representing the most recently recorded cardiac data. In one embodiment, the R-R plot can be displayed with markers, such as a bar spanning a length of time, to identify those sections of the R-R plot that correspond with daytime or nighttime. For example, a bar 193 can be positioned under the R-R trace to indicate those R-R values obtained during a predetermined time, such as at night or hours when an individual sleeps. Such markers can be helpful since the average heartrate decreases during periods of sleep and the marker indicates the reason for the decrease. Other markers can be added to the R-R overview plot, in addition to or in lieu of the daytime/nighttime markers, such as markers for each 24 hour period or times during which a patient has previously experienced a cardiac event.

The displayed R-R plot overview 183 can also include one or more indicators for information related to the cardiac data, such as user identified cardiac events. Each of the indicators can be displayed as a flag or box, and a letter, number, word, or symbol within the flag or box can identify a type of indicator being entered. In one example, a circle indicator 191 can be used to identify when a user presses button on the ambulatory ECG monitor to indicate a cardiac event, such as when the patient experiences a heart flutter, arrhythmia, shortness of breath, or any other cardiorespiratory discomfort. Specifically, the circle indicator 191 can be added to the overview R-R plot 183 to identify a time at which the cardiac event occurred and to provide a picture of the patient's cardiac data results at the time of the button press. Data identifying the button press can be transmitted wirelessly upon the press or uploaded from the wearable ambulatory ECG monitor after recording has terminated.

Additionally, indicators can also be used to identify a time and event notated by the patient via an electronic journal entry. For example, a patient can maintain an electronic journal in which cardiac events, such as a heart flutter, arrhythmia, shortness of breath or any other cardiorespiratory discomfort experienced by the patient, can be entered. For example, a journal entry can be associated with a letter "D" indicator 195. A time at which the journal entry was generated can be used to place the letter "D" indicator in the R-R plot. Alternatively, a time at which the patient identifies that the cardiac event occurred via the journal entry can be used to place the indicator.

Indicators can also be used to identify noise within the R-R plot or ECG trace. Prior to display, the cardiac data of the overview R-R plot can be analyzed to identify noise, such as due to electrode contact, baseline drift, or instrumentation noise, as well as other types of noise. A presence of noise in an R-R plot or ECG trace data can lead to incorrect diagnoses. Accordingly, noise can be filtered from the R-R interval plot, or identified and marked to indicate noise. The noise can be identified by a reviewer or automatically via a classifier or artificial intelligence, such as by machine learning or based on one or more thresholds. The reviewer can be a medical professional or another individual that is trained to read cardiac data. Further, the data can be reviewed via artificial intelligence to identify noise, as described in commonly-owned U.S. Pat. No. 10,251,576, issued Apr. 9, 2019, which is hereby incorporated by reference in its entirety. The reviewer reviews the data provided in the R-R plot and ECG traces to identify events of interest that can be provided to a medical professional for use in diagnosing the patient, as further described below.

Once identified, the noise can be removed or can be included in the plot and marked to identify the corresponding data as noise. For example, the data points associated with noise can be a different color than data associated with no noise, can be highlighted, or associated with an indicator, such as a word, number, or symbol to identify the noise.

A physician, nurse, or other medical professional, as well as a trained cardiac data reviewer can interact with the data of the R-R plot by zooming in and out of particular portions of interest to increase or decrease a level of detail provided by the plot. For example, the user can zoom into a portion of the plot to obtain additional data by moving a roller located on a computer mouse, for example. However, other mechanisms for zooming in and out of a display are possible. The zooming, both in and out, of a particular area of interest in the plot can be continuous, rather than based on predefined values to ensure that the data scale needed is available. Continuous zooming also provides a smoother zooming movement than a zoom action based on predefined zoom levels.

Since zooming in increases a granularity of the data points in the plot at a location of interest and data points surrounding the location of interest, the amount of data in the overview R-R plot may exceed the dimensions of the display screen upon zooming and thus, those data points located further from the location of interest may be removed from the display. Generally, the zooming in function is similar to increasing a view of an object under a microscope and omitting part of the peripheral views as the view of the object increases in magnification. For a graph, the data points to be removed from the display are generally determined based on a distance from the location of interest and the display size, and the removed data points can include those that are located on all sides of the data points associated with the location of interest. Accordingly, with respect to the R-R plot, data points for cardiac data occurring immediately prior to or after the data points at the location of interest can be removed based on the granularity of the data the location of interest. Thus, the displayed data in the R-R plot can be discontinuous. Removing such data points can lead to a misdiagnosis since a user is unable to see the data points surrounding the location of interest, which may represent a cardiac event.

Figure 16:
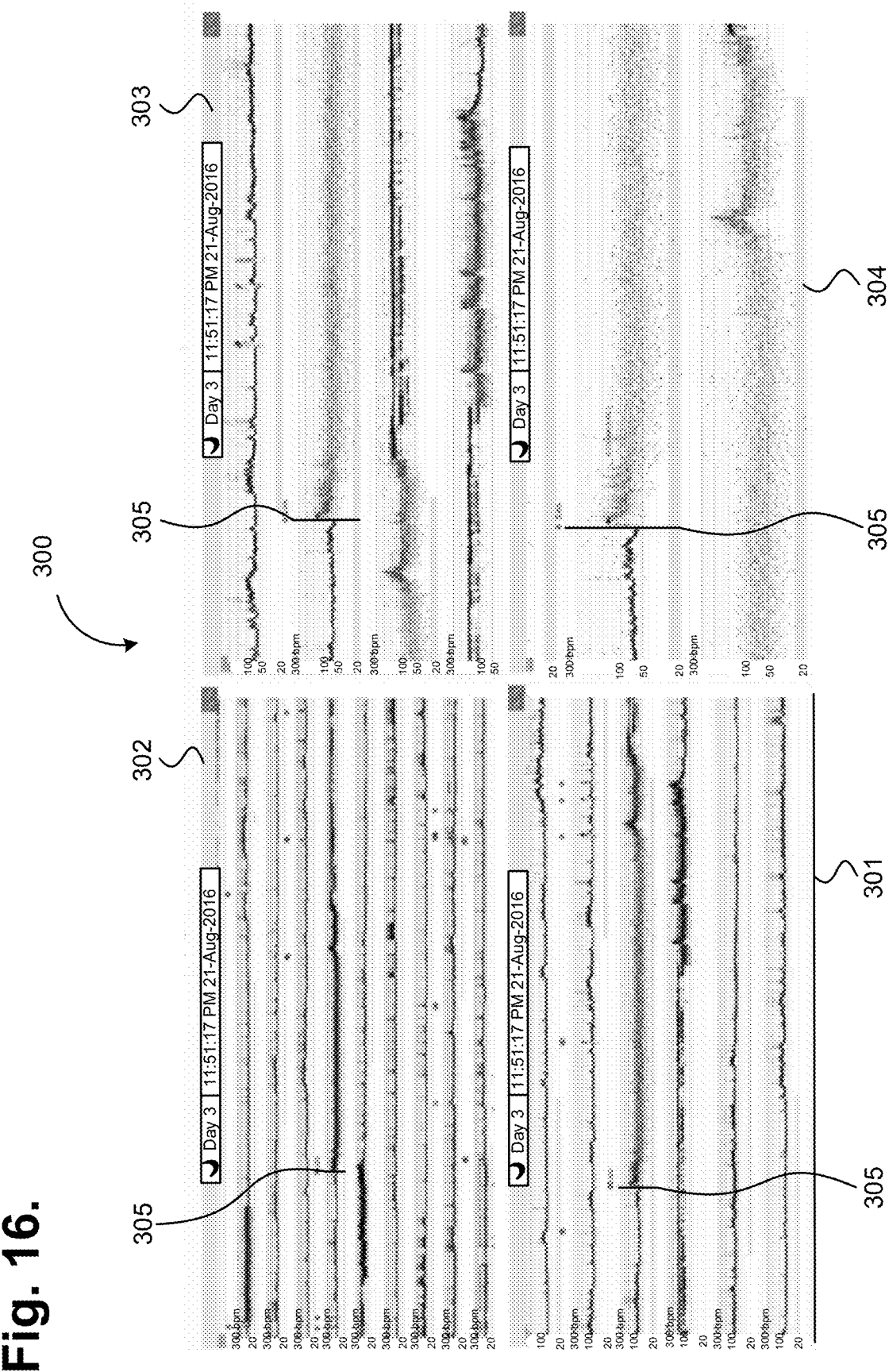
FIG. 16 is a diagram showing, by way of example, data zooming.

To prevent removal of the data points preceding or following the data points that correspond with the location of interest, the zooming function can occur as a sliding action, rather than as a telescoping action. FIG. 16 is a diagram 300 showing, by way of example, data zooming. Four frames 301-304 each showing a different amount and detail of R-R data are displayed to provide an example of the data zooming. An original R-R plot 301, such as displayed above in FIG. 15, provides R-R data points. As shown in a zoomed out data plot 302, a user zooms out at a point located in the plot 301 represented by a line indicator 305, which is positioned at a location in the plot that includes a button press and a diary entry. The point 305 can be used as a point of reference during the zooming. Zooming out provides additional data points, not included in the original R-R plot, taken over time periods, also not included in the original R-R plot. Conversely, zooming in removes the data points that were recorded the earliest and the latest to ensure that the displayed data points are continuous after zooming, as displayed in zoomed R-R plots 303 and 304.

For instance, upon receiving instructions to zoom into a portion of the R-R plot, a location of interest on the plot is identified by a user or automatically using artificial intelligence or a classifier. Subsequently, the data points associated with the location of interest are magnified or the granularity of the data increases. As the granularity of the data points increases, the display is likely unable to display the same amount of data due to size constraints of the display. To ensure that data located near the data associated with the location of interest is maintained and not removed, the data points associated with the earliest recorded data and the latest recorded data are removed first. For example, the earliest recorded data can be located in an upper left corner of the plot and can move left along the row until removed from the display, as the granularity of the data at the location of interest increases. At the same time or a different time, the most recently recorded data, which can be located in a lower right corner of the plot, can slide to the right along the row until out of the size constraints of the display. Accordingly, since the earliest and most recent data is removed first, the data associated with the location of interest remains in the display. The more a user zooms into the R-R data points, the more detail is provided about the data points displayed. For example, individual data points are more easily identifiable in the plot 304 that is more zoomed in.

Within the R-R plot, cardiac events can be identified automatically or via a reviewer and used to generate a strip of R-R data. In one example, an event can be identified via artificial intelligence, such as described in detail in U.S. Pat. No. 10,463,269, issued Nov. 5, 2019, which is hereby incorporated by reference, and a strip for the event is generated based on R-R data occurring prior to, during, and after the event to provide medical professionals with a screenshot of the patient's cardiac data and condition prior to, during, and after the event occurrence. Each strip of R-R data generated using artificial intelligence can be saved as a report strip with different ECG trace plots. In one example, the report strips can include an eight second ECG trace for the near field view, a 56 second ECG trace for the intermediate field view, and a 40 minute R-R plot from the overview R-R plot. However, other time durations are possible. In one embodiment, each strip can include data recorded over the same amount of time. Further, each strip of R-R data can be automatically classified as a particular rhythm type or cardiac event via artificial intelligence. The classification of the R-R strip can be assigned to the report strip in which the R-R strip is included. The data associated with the saved report strip can be associated with a link to the saved strip within a generated report or in a different location within the user interface.

Figure 17:
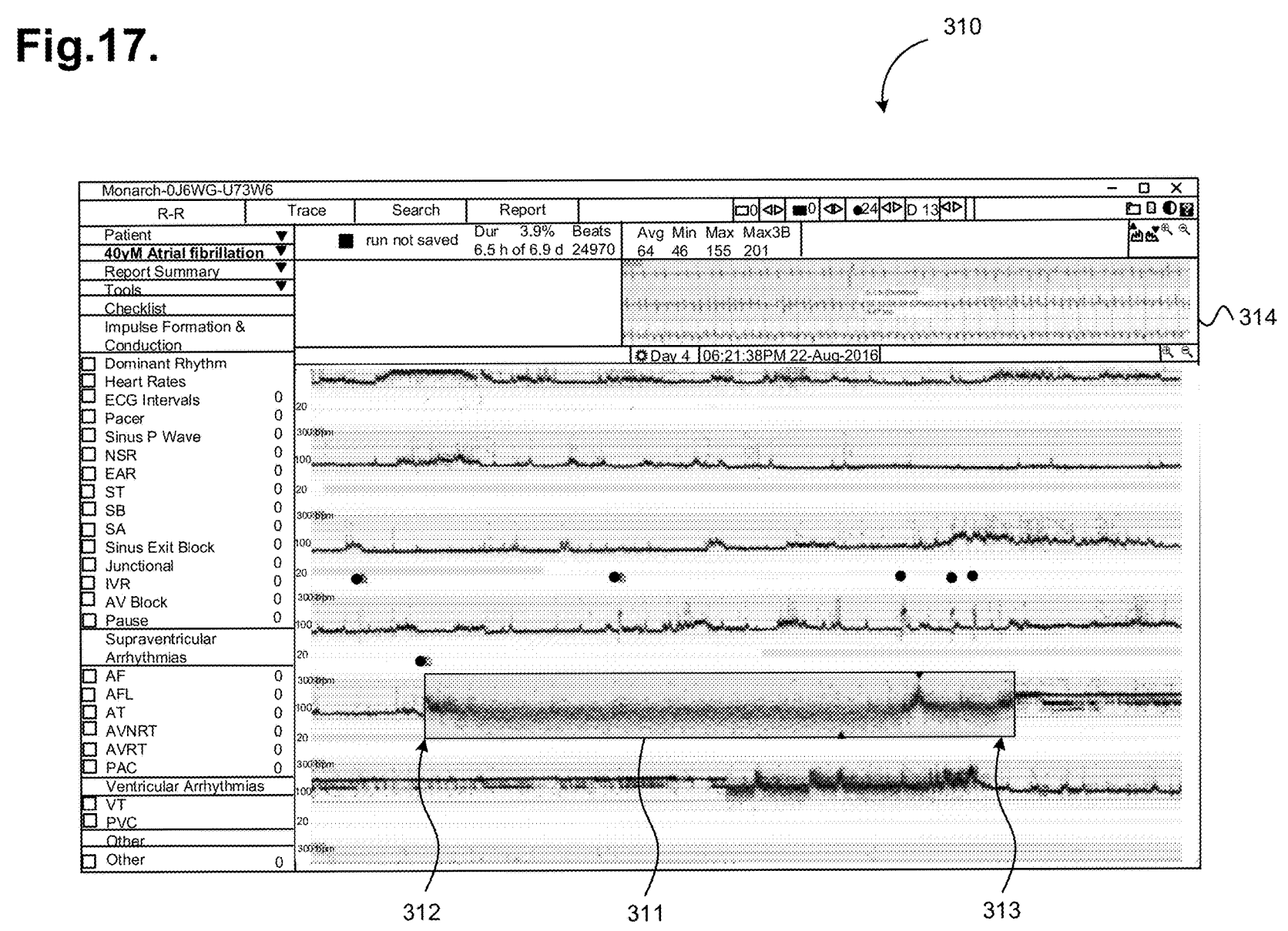

Additionally, or in lieu of artificial intelligence, the reviewer can manually identify sections of the R-R plot for use in generating a run of data points of interest. FIG. 17 is a diagram showing, by way of example, an interactive user interface 310 for generating a run of data. The user can select a set of R-R data points within the overview R-R plot that are of interest, such as data reflecting a cardiac event, as well as data prior to and after the event, to generate the run 311. In one embodiment, a user can click a mouse, use a verbal command, or utilize a touch screen to identify a location of a cursor within the R-R plot to mark a beginning 312 and an end of the run 313. For example, a user can left click a mouse and at a beginning 312 of the run and drag the mouse over the R-R data points until an end 313 of the run when the user releases the right mouse button. However, other methods for generating the run are possible. The run can be highlighted to identify the data points included in the run. The mid-length ECG trace plot 314 stays in sync with the R-R plot, so the run 311 is shown in both panels and can be adjusted in either panel. For example, adjusting the onset and offset in the mid-length ECG trace plot 314 can provide more exact positions based on the more detailed run. Each run can be classified and saved.

Figure 18:
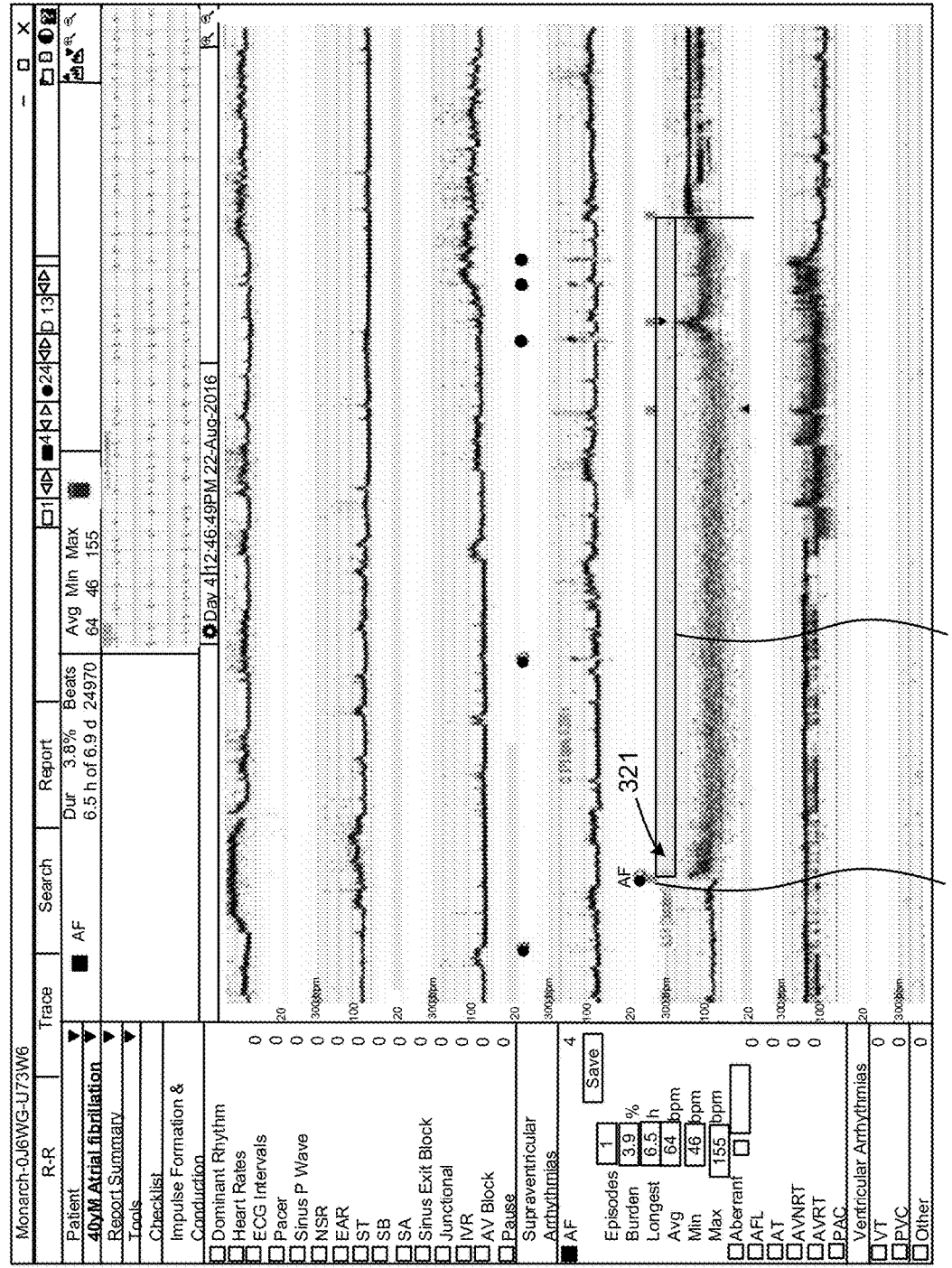
FIG. 18 is a diagram showing, by way of example, an interactive user interface for displaying a classified run of data.

FIG. 18 is a diagram showing, by way of example, an interactive user interface 320 for displaying a classified run of data. Each run, including the run 311 described above with respect to FIG. 17 can be assigned an identifier, such as a number, name, or symbol 191 to identify the run. Additionally or in lieu of the identifier, the run 311 can include highlighting or a bar that runs along the data points in the run, such as above or below, to identify the run. Such identifiers can also be placed in the short and mid-view ECG trace plots. Further, the bar or highlighting representing the run 311 can be one color, while the bar or highlighting representing an automatically determined strip of R-R data points can be a different color.

Once generated, each run can be annotated with a rhythm type represented by the cardiac data in that run. For example, the run 311 of R-R interval data represents AF 321 by a dispersed cloud of dots (Gaussian-like distribution) without a discernible main heart rate line representing regular heartbeats, as described above in detail with respect to FIG. 10. The AF classification 321 can be assigned by a reviewer or automatically determined, and is assigned to the run and noted in the overview R-R plot by assigning a marker for AF to the run. Other rhythm types used to classify the strips can include Atrial Fibrillation, Atrial Flutter, Atrial Tachycardia, Atrioventricular Nodal Reentry Tachycardia, Atrioventricular Reentrant Tachycardia, SV Aberration, Idioventricular Rhythm, Sinus Bradycardia, Sinoatrial node, Premature Atrial Contraction, Sinus Exit Block, Junctional, AV Block, and Longest Pause. However, other types of cardiac rhythms and rhythm measurements are possible for classifying the report strips. Additionally, the runs that are saved to a database can be associated with a saved symbol 322 to indicate that the run has been saved. The cardiac data associated with saved runs can be analyzed to provide a summary of cardiac measurements, as described in detail below with respect to FIG. 19. Further, the data of each saved run can include a link directly to the saved run located in a report or a different location of the user interface.

In a further embodiment, runs that are automatically determined via a classifier or artificial intelligence can be reviewed by users and edited. Any edits to a run can be provided as feedback for improving algorithms executed by the classifier or artificial intelligence. The system can also keep track of manually marked runs to use for improving the automatic algorithms. Further, all edits can be tracked and maintained, including information such as who made the edit, when the edit was made, and information the edit included.

Figure 19:
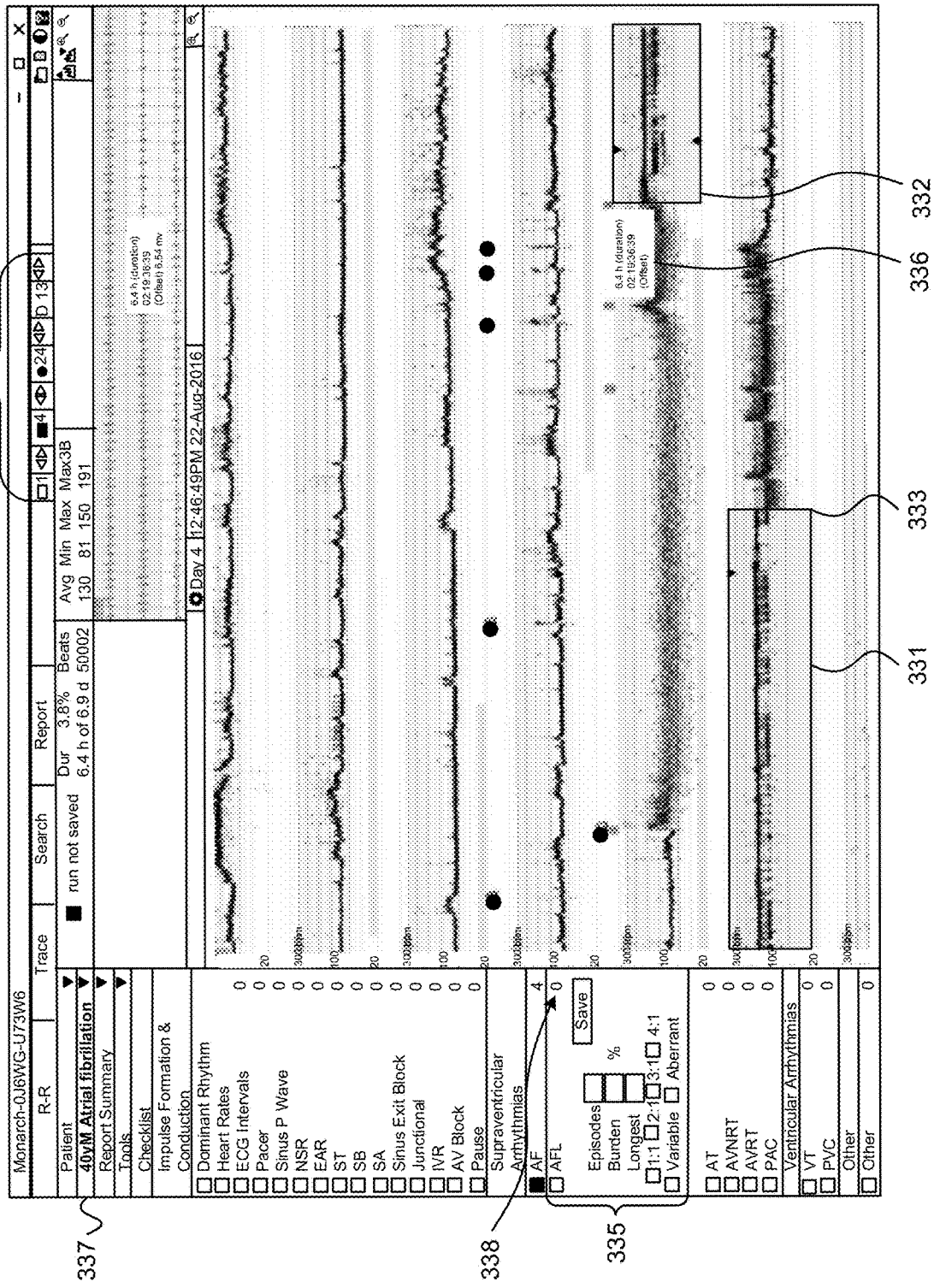
FIG. 19 is a diagram showing, by way of example, an interactive user interface generating a further run of data points.

Other cardiac rhythm types can be classified in additional runs. For example, FIG. 19 is a diagram showing, by way of example, an interactive user interface 330 generating a further run of data points. The run 331 occurs after the AF run described above with respect to FIG. 18 and is defined by a beginning 332 and an end 333 of the run. To manually classify and save the run 333, a user can select the correct rhythm type from a list of rhythm types 335 in the patient summary bar 337 and select a save button. However, the run can also be classified automatically and in one embodiment can be reviewed and possibly revised by the user. Once the run has been classified and saved, a number of occurrences 338 for the classified rhythm type, here AFL, can be increased by one occurrence. The number of occurrences 338 can be displayed in the patient summary bar and associated with the rhythm type.

Upon generating a run of data points, a set of cardiac rhythm measurements can be automatically calculated based on the cardiac data points that fall within the start and end points of the run. The cardiac rhythm measurements can include a length of the run, offset, number of episodes of the event identified in the run, the burden, longest episode, average heart beats per minute (bpm), minimum bpm, and maximum bpm. However, other cardiac rhythm measurements are possible, such as fastest heart rate and longest duration heart rate. One or more of the cardiac measurements can be displayed in a pop up notification 336 adjacent to the run, while one or more of the measurements can be displayed in the patient summary bar 337, such as under the classified rhythm type 335. In one embodiment, the measurements can be based on a 30 second window of data points in the run. Alternatively, each 30 second segment in the run is calculated to find the specific measurements. Other methods for computing a fastest or maximum heart rate are possible, such as finding the maximum average heart rate as computed over 30-second windows across the data set. The 30-second average is useful for a general average heart rate. Another computation method is finding the maximum heart rate as computed over 3-beat windows across the data set. The 3-beat average is useful for finding the fastest region of tachycardia runs. The "windows" across the data set are incremented such that they overlap, such as to find the actual max anywhere in the data, rather than sequentially aligned next to each other, which would give a false answer since the max would depend on where the next sequence starts/stops.

Figure 20:
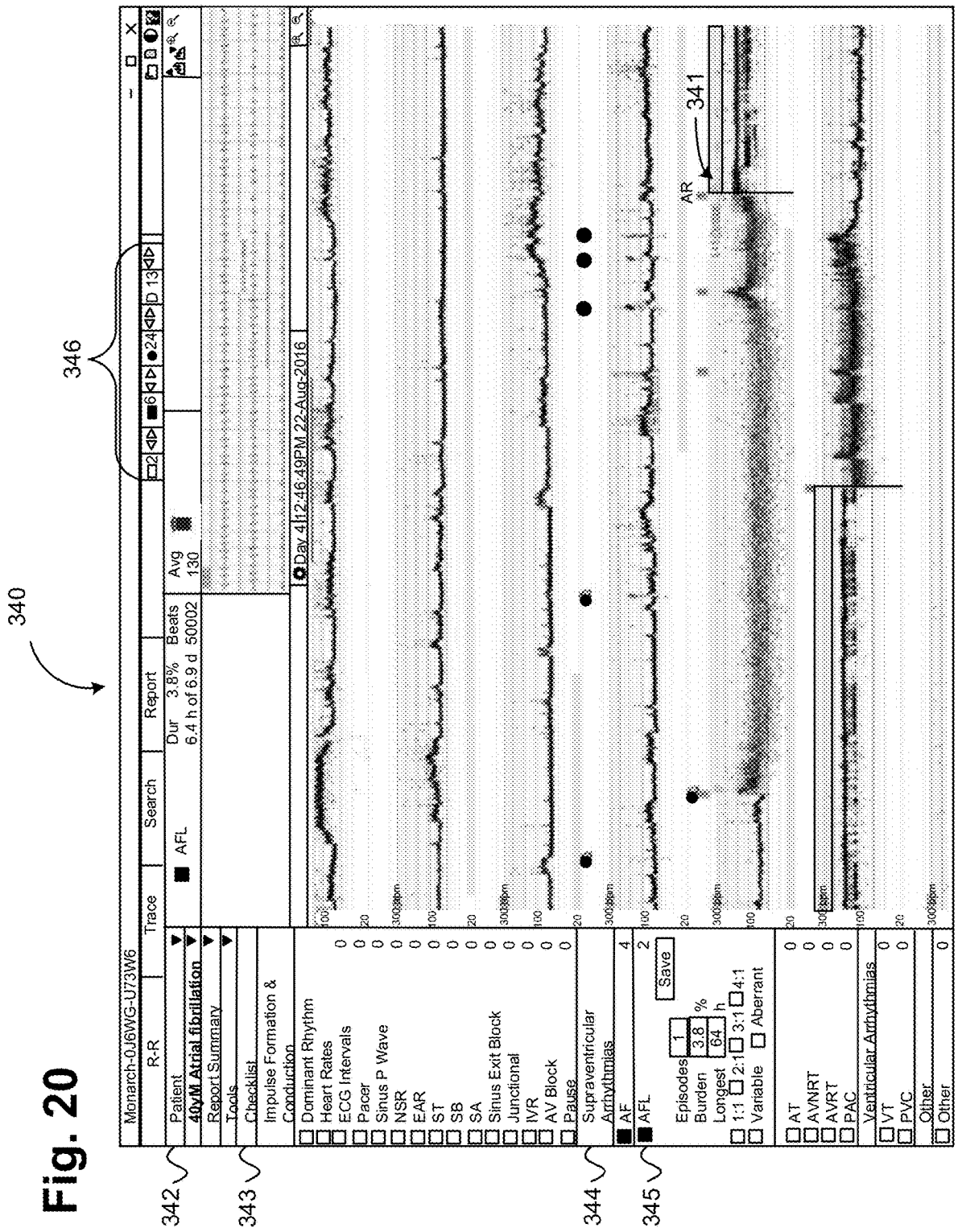
FIG. 20 is a diagram showing, by way of example, an interactive user interface for assigning a classification to the further run of FIG. 19.

Subsequently, the run 331 can be classified as described with respect to FIG. 20, which provides a diagram showing, by way of example, an interactive user interface 340 for assigning a classification to the further run of FIG. 19. For example, the run includes a dense line of R-R data points representing firm 3:1 atrial flutter, as described above with respect to FIG. 8, and is assigned a classification of atrial flutter 341.

After classification, the runs associated with each rhythm type can be calculated and stored. The cardiac rhythm measurements can be determined across all the runs and automatically generated data strips obtained from the overview R-R plot to provide a summary of the events of interest and cardiac rhythms. The report strips and associated rhythm cardiac factors can be collected and provided in a diagnostic report for the patient, as further described below with respect to FIGS. 18 and 19.

The cardiac rhythm classifications and cardiac rhythm measurements can be displayed in the patient summary bar 342, which provides summary data based on the cardiac rhythm factors determined from the runs and data strips.

Specifically, the patient summary offers a medical professional or reviewer, such as an ECG technician with a quick overview of rhythms experienced by the patient during the recording period. The patient summary bar 342 can include patient identification information, including patient name or identification number, and date of birth. Other types of patient identification information are possible. The patient summary bar can also include a checklist 343 of cardiac rhythm patterns, which can be categorized as cardiac summary, supraventricular, impulse, ventricular, device, and other. Each category 344 can be associated with one or more cardiac rhythm types 345. For example, a cardiac summary category can be associated with normal sinus rhythm, bifid P-wave, ectopic atrial rhythm, and pre-excitation, while a supra ventricular category can be associated with atrial fibrillation, atrial flutter, atrial tachycardia, atrioventricular nodal reentry tachycardia, atrioventricular reentrant tachycardia, and SV aberration. Other categories and associated rhythm types are possible. Each rhythm type 345 can be displayed under the appropriate category 344 with a number of occurrences of that rhythm experienced by the patient. Listing each type of cardiac rhythm can help ensure a medical professional or reviewer that the rhythm was considered, but not identified within the overview R-R plot.

Each category can be associated with a number of runs or data strips for each rhythm type for that category. For example, there are 6 events of supraventricular rhythms, including 4 instances of atrial fibrillation and 2 events of atrial flutter. Upon selection of one of the rhythm types 345 in the patient summary bar 342, such as atrial fibrillation, further information can be displayed, including a number of strips with that rhythm type, a number of episodes of that rhythm type, a duration of the longest episode, minimum heart rate, maximum heart rate, and average heart rate. Other types of information are possible. Further, the number of runs and strips, as well as button presses and diary entries can be totaled and displayed via a field box 346 for quick review.

Figure 21:
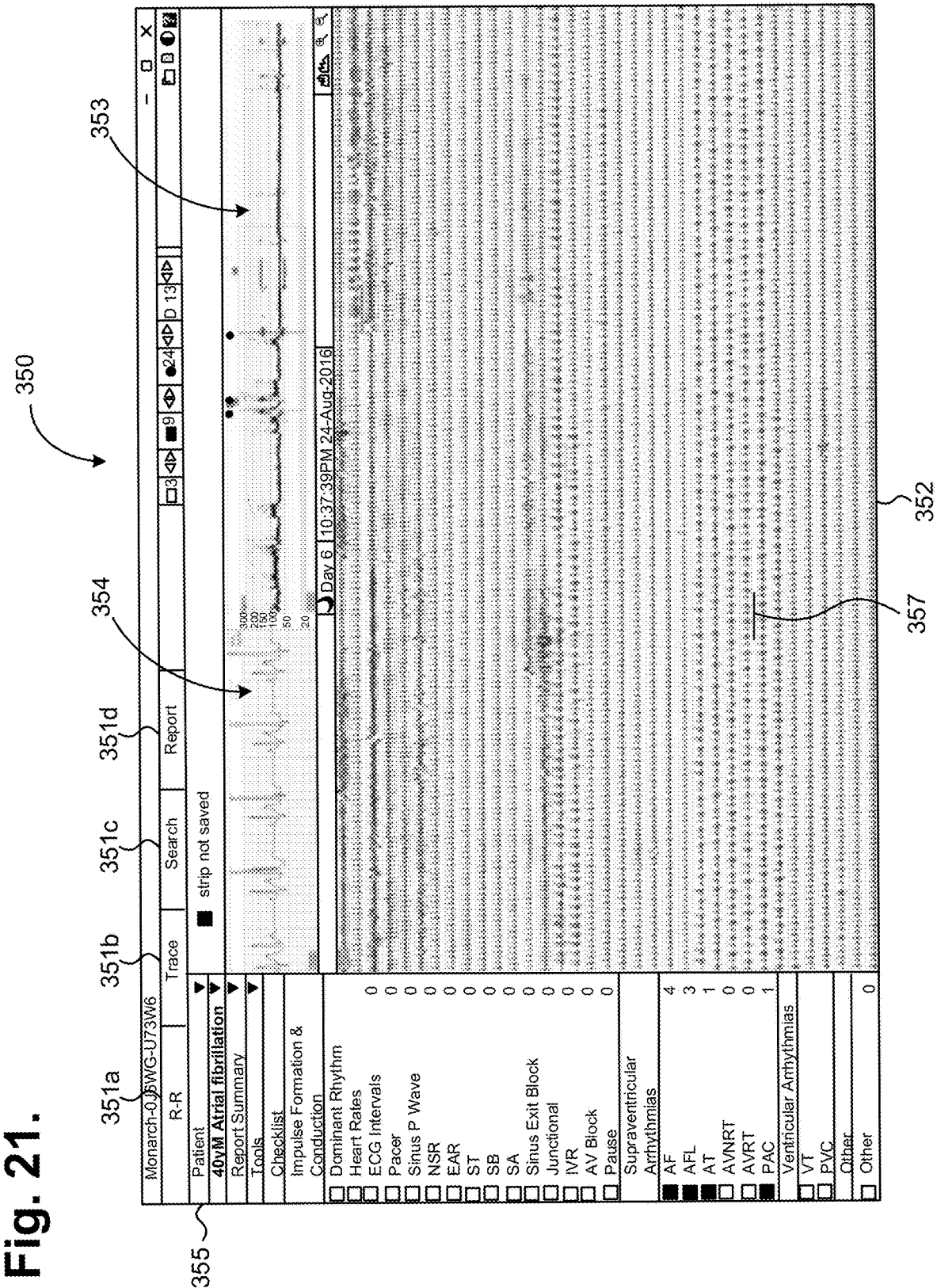
FIG. 21 is a screenshot of an interactive user interface for displaying an overview ECG trace plot.

Returning to FIG. 15, the web page 180 can also include an overview ECG trace Users, such as medical professionals or reviewers can access different views of the cardiac data recorded by the wearable ambulatory ECG monitor to facilitate diagnosis of the patient. FIG. 21 is a screenshot of an interactive user interface 350 for displaying an overview ECG trace plot 201. The interactive user interface can be implemented via a web page or software application. The web page 350 can include tabs 351a-d for an overview R-R plot web page 351a, trace plot 351b, search 351c, and report 351d. The web page 350 associated with the trace plot tab 351b can include an overview ECG trace plot 352, a portion of the ECG trace plot 354, an R-R plot 353 representing a portion of the overview ECG trace plot, and a patient summary bar 355.

The overview ECG trace plot 352 can include ECG data recorded for a predetermined amount of time or recorded over the life of the wearable ambulatory ECG monitor. As described above with respect to the R-R data points of FIG. 15, the ECG trace can be displayed along horizontal rows that continuously wrap from left to right and top to bottom to fill the display. The earliest recorded data can be provided in a top left corner and the most recently recorded data can be located in a bottom right corner of the display. However, other displays of the data are possible.

Figure 22:
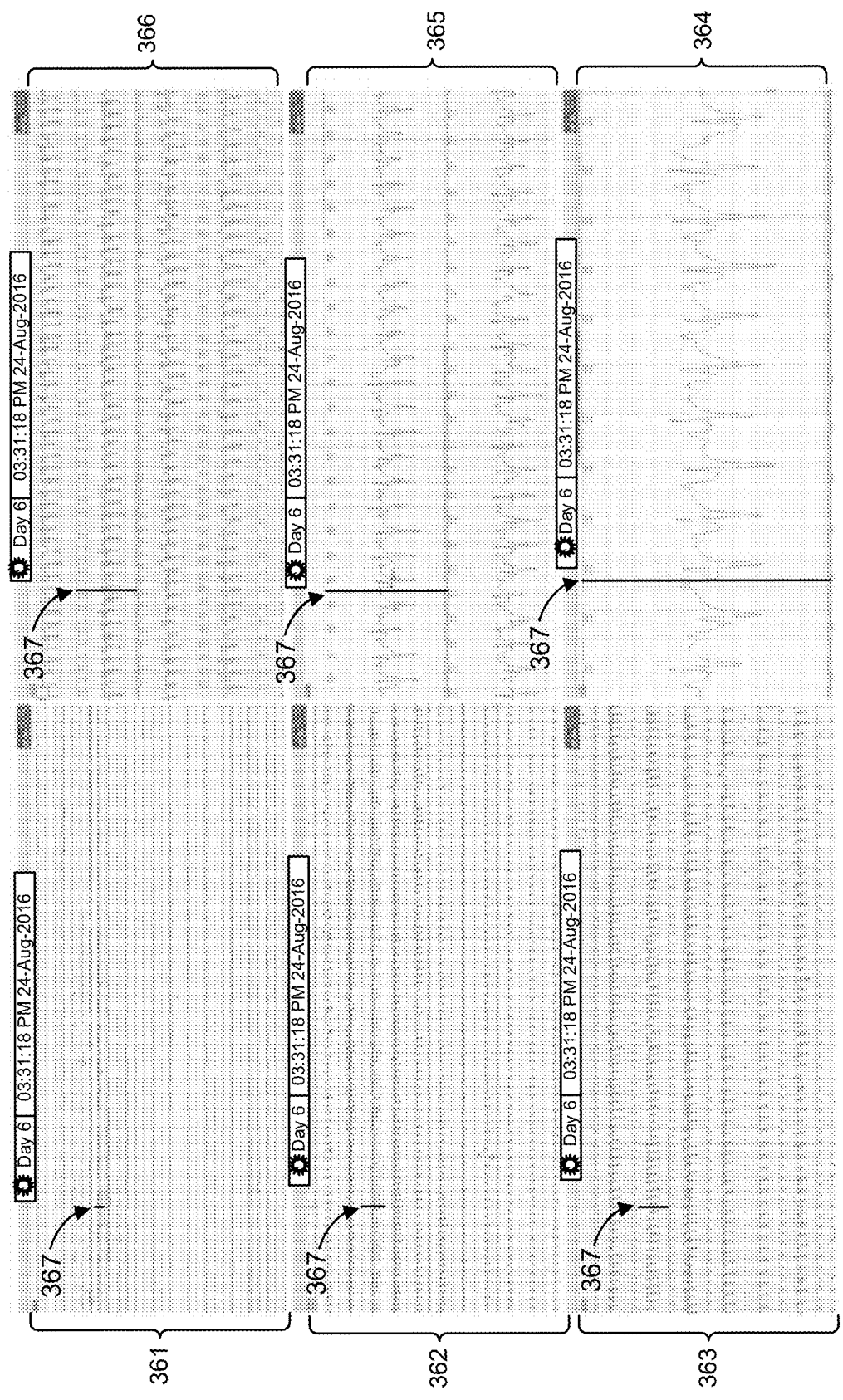
FIG. 22 is a diagram showing, by way of example, data zooming of the ECG trace plot of FIG. 21.

Users can zoom in and out of the trace data to obtain further detail. FIG. 22 is a diagram showing, by way of example, data zooming 360 of the ECG trace plot of FIG. 21. The diagram includes six different views 361-366 of the ECG trace plot at different stages of zoom. A first view of the ECG trace plot corresponds to the ECG trace plot as described above with respect to FIG. 21 with a point of focus 367, at which zooming into the data will occur. The point of focus 367 can be displayed via a line, dot, circle, or other marker. Upon zooming into the ECG trace, data that was collected at a beginning of recording and most recently is removed from the display 362 to provide further detail with respect to the ECG trace remaining in the display. Further, as additional zooming occurs at the point of focus 367, further detail is provided about the information closest to the point of interest 367, as displayed 363-366.

Figure 23:
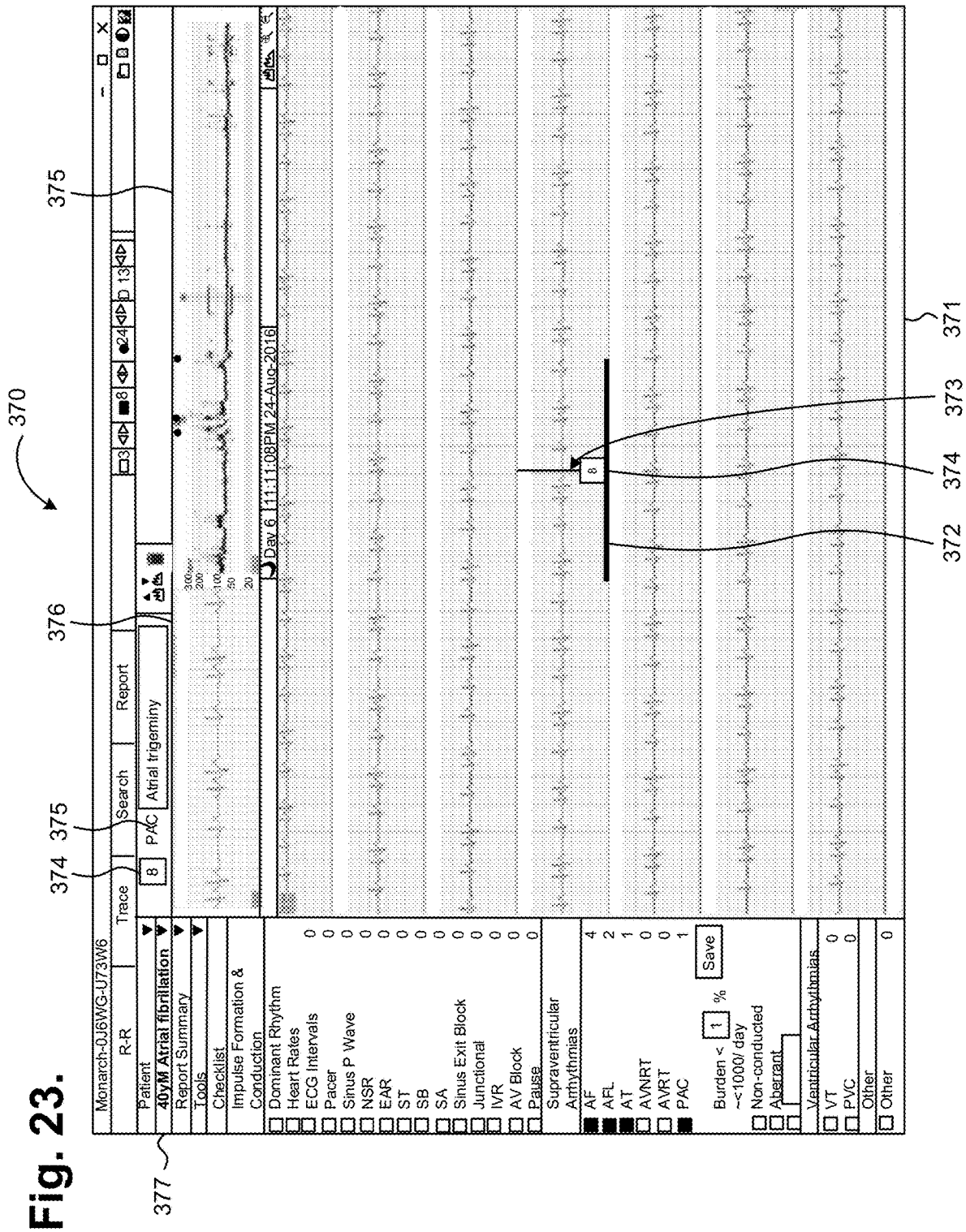
FIG. 23 is a diagram showing, by way of example, an interactive user interface for displaying a selected data strip.

A reviewer can interact with the displayed ECG trace data. FIG. 23 is a diagram showing, by way of example, an interactive user interface 370 for displaying a selected data strip 372. The interface 370 displays an overview ECG trace 371, a portion of the R-R trace 375 that corresponds with the displayed ECG trace 371, a short-view ECG trace 376, and a patient summary bar 377. The data displayed via the short-view ECG can be selected based on an identified cardiac event in the overview ECG trace, as described below.

Each of the short-view ECG 376, R-R plot 375, and overview ECG trace 371 can be manipulated by a user, such as a medical data reviewer or analyzed automatically to obtain data for presenting to a medical professional for diagnosis. As described above, segments of the cardiac data can be selected manually as runs or automatically as data strips to obtain data about cardiac events experienced by the patient. In one embodiment, the manually selected runs can each include data collected over different lengths of time, while the automatic data strips each include data collected over a predetermined amount of time. The automatic data strips can be recognized via artificial intelligence based on an identified cardiac event. Each automatic data strip can be recognized via a data marker 372, such as a line or bar, which can identify a range of data included in that strip. In one example, as the strip can cover an eight second duration of time; however, other durations are possible as identified automatically or via a user. For instance, the marker 372 can include upper and lower bounds to indicate a duration of time which is associated with a portion of the overview ECG trace plot 371. In one example, a cardiac event identified by the artificial intelligence can be identified as a center 374 of the data strip and a predetermined duration of time prior to and after the center of the identified center is determined for inclusion in the strip. Each strip can be assigned a rhythm classification 378 and an identifier 374.

Users can navigate between the short-view ECG trace 376, the R-R plot 375, and the overview ECG trace plot 371. For example, a user can select a point within the R-R plot 375, such as via a cursor, and the same position can be identified in the overview ECG trace plot 371. Additionally, users can select a point within the overview ECG trace plot and the same position can be identified in the R-R plot.

Figure 24:
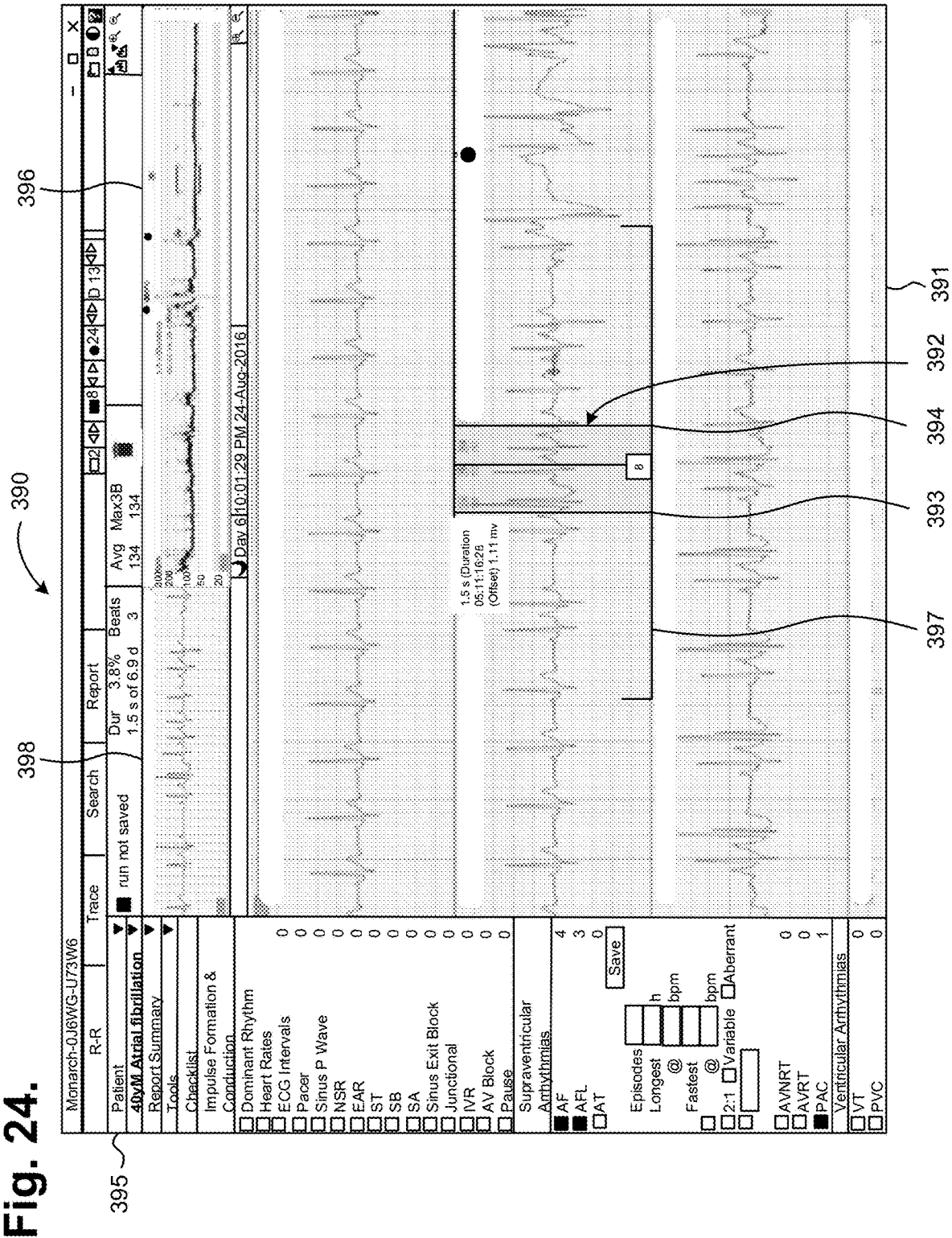
FIG. 24 is a diagram showing, by way of example, an interactive user interface for generating a run of ECG trace data.

Runs of cardiac data can also be generated manually by a reviewer or other user via the overview ECG trace. FIG. 24 is a diagram showing, by way of example, an interactive user interface 390 for generating a run of ECG trace data 391.

The user interface 390 can include a patient summary bar 395, a short-view ECG trace 398, an R-R plot 396, and an overview ECG trace 391. Within the overview ECG trace 391, a user can place markers at a beginning 393 and an end 394 of a strip of data to generate a run 392, as described above in detail with respect to FIG. 17. Each run can include an indicator, such as highlighting or a bar to span a length of the run. Further, the run can be generated anywhere within the overview ECG trace 391, including within a data strip identified via artificial intelligence 397.

Figure 25:
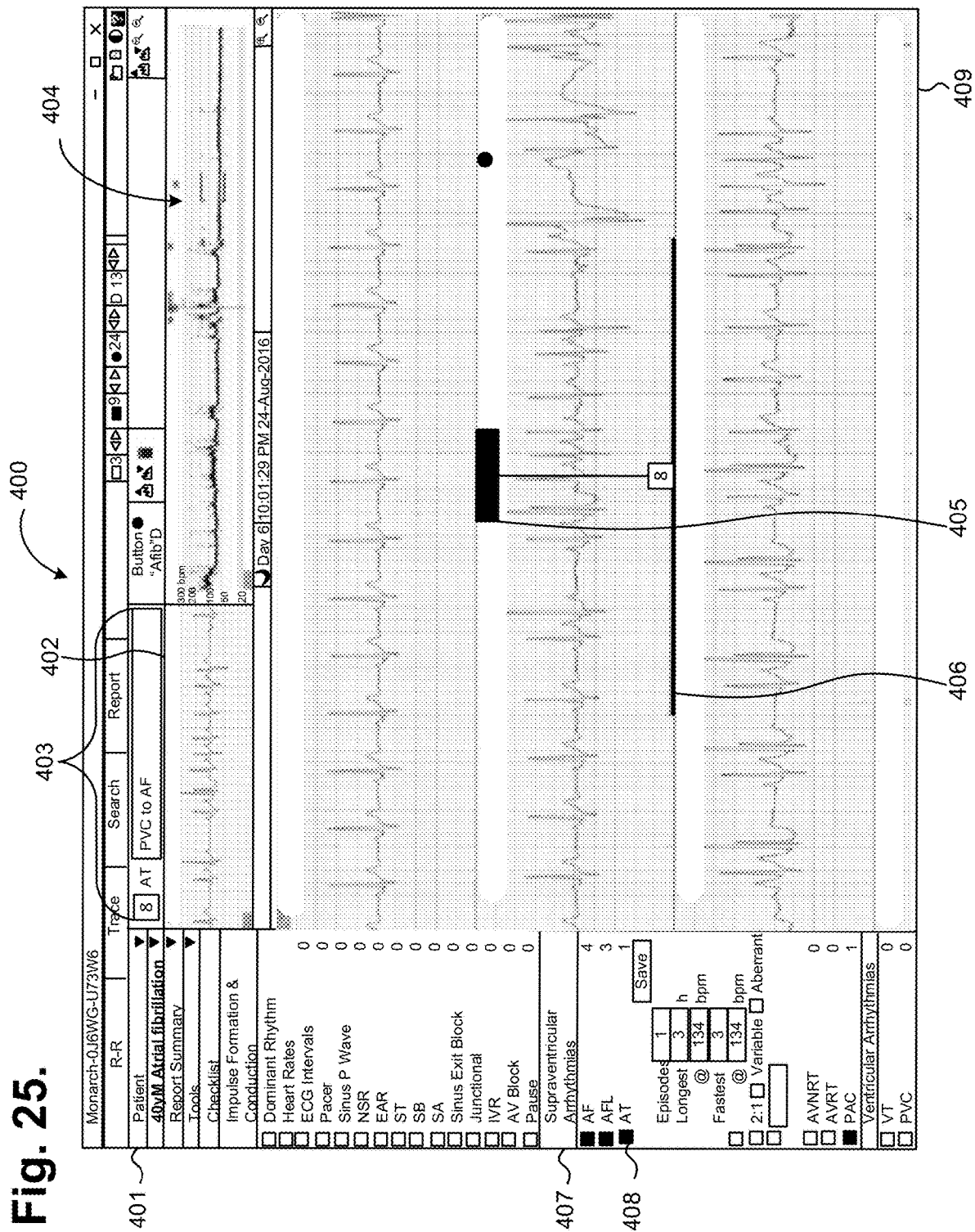
FIG. 25 is a diagram showing, by way of example, an interactive user interface for saving a run of ECG trace data.

Once generated, the run can be classified and saved. FIG. 25 is a diagram showing, by way of example, an interactive user interface 400 for saving a run of ECG trace data. The user interface 400 can include a patient summary bar 401, a detailed data segment 403, which provide information about a run of data or a data strip, a short-view ECG trace, a portion of an R-R plot 404, and an overview ECG trace 409. The ECG trace 409 includes markers for a data strip 406 and a run 405. The run, as generated and described above with respect to FIG. 24, can be saved via a user, such as by a "save button" (not shown), and classified with a rhythm type, such as Atrial Tachycardia. The status of the run and the classified rhythm type can be displayed in the detailed data segment 403. Also, the run 405 can be identified via a bar that spans a distance of the run.

Figure 26:
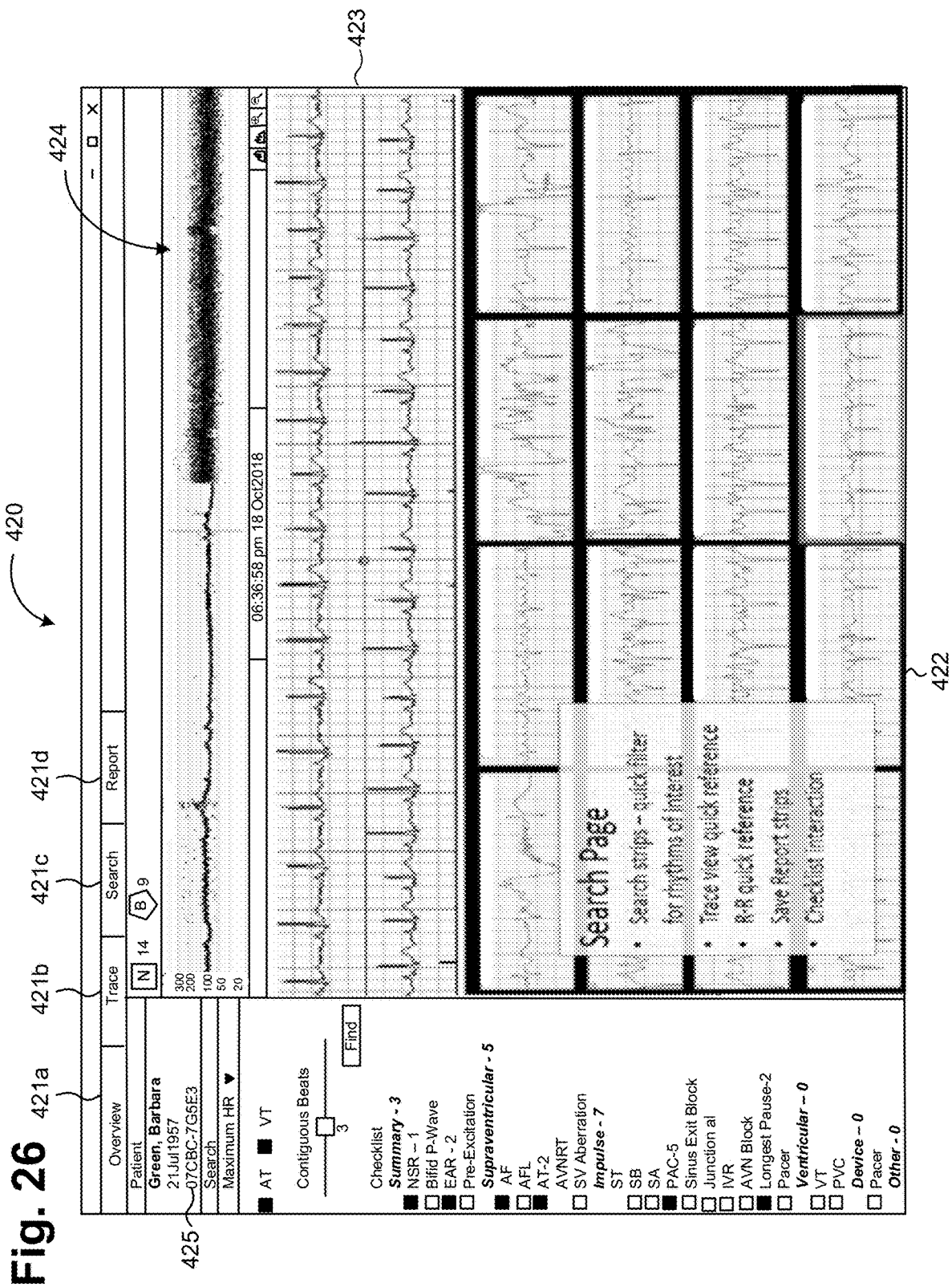
FIG. 26 is a diagram of an interactive user interface for conducting a search for cardiac events.

Once the runs and data strips are classified and saved by rhythm type, a user can select one or more of the categories 407 of rhythm types or individual rhythm types 408 in the patient summary bar 401 by selecting a particular category 407 or rhythm type 408. Upon selection of the category or rhythm type, all the data strips or runs classified as that category or rhythm type can be highlighted within either the overview R-R plot or overview ECG trace, and displayed. FIG. 26 is a diagram of an interactive user interface 420 for conducting a search for cardiac events. The interface, such as implemented via a web page 420 can include tabs 421a-d for an overview R-R plot web page 421a, trace plot 421b, cardiac event search 421c, and report 421d. The web page 420 associated with the search tab 421c can include rhythm search results 422, a partial trace ECG 423, a partial R-R plot 424, and a patient summary bar 425. A user can enter a search query by selecting one or more of the categories or rhythm types within the patient summary bar 425 to identify those runs or data strips that satisfy the selected category or rhythm type. Additionally, a user can enter a search value for minimum or maximum heart rate, average heart rate, or contiguous beats or other search fields provided in the patient summary bar.

Results of the search include runs or data strips that satisfy the query and can be displayed in the results section 422. Further, a selected result is displayed via the partial trace ECG 423 and within the R-R plot 424. Specifically, as you select a rhythm strip from the search results, the corresponding area in the partial trace ECG and R-R plots can be highlighted or if necessary, the partial trace ECG and R-R plot can be updated to include the selected rhythm strip.

The search tool could be provided as a separate tab, as described above, or integrated into the other tabs. In all views, a list of search results strips are identified and the run associated with the search finding is highlighted. For example, if a search found a run of 12 beats of Ventricular Tachycardia, clicking on that search strip would show the run in the partial trace ECG and R-R plot, and the 12 beat region would be highlighted with a run that can be saved.

Figure 27:
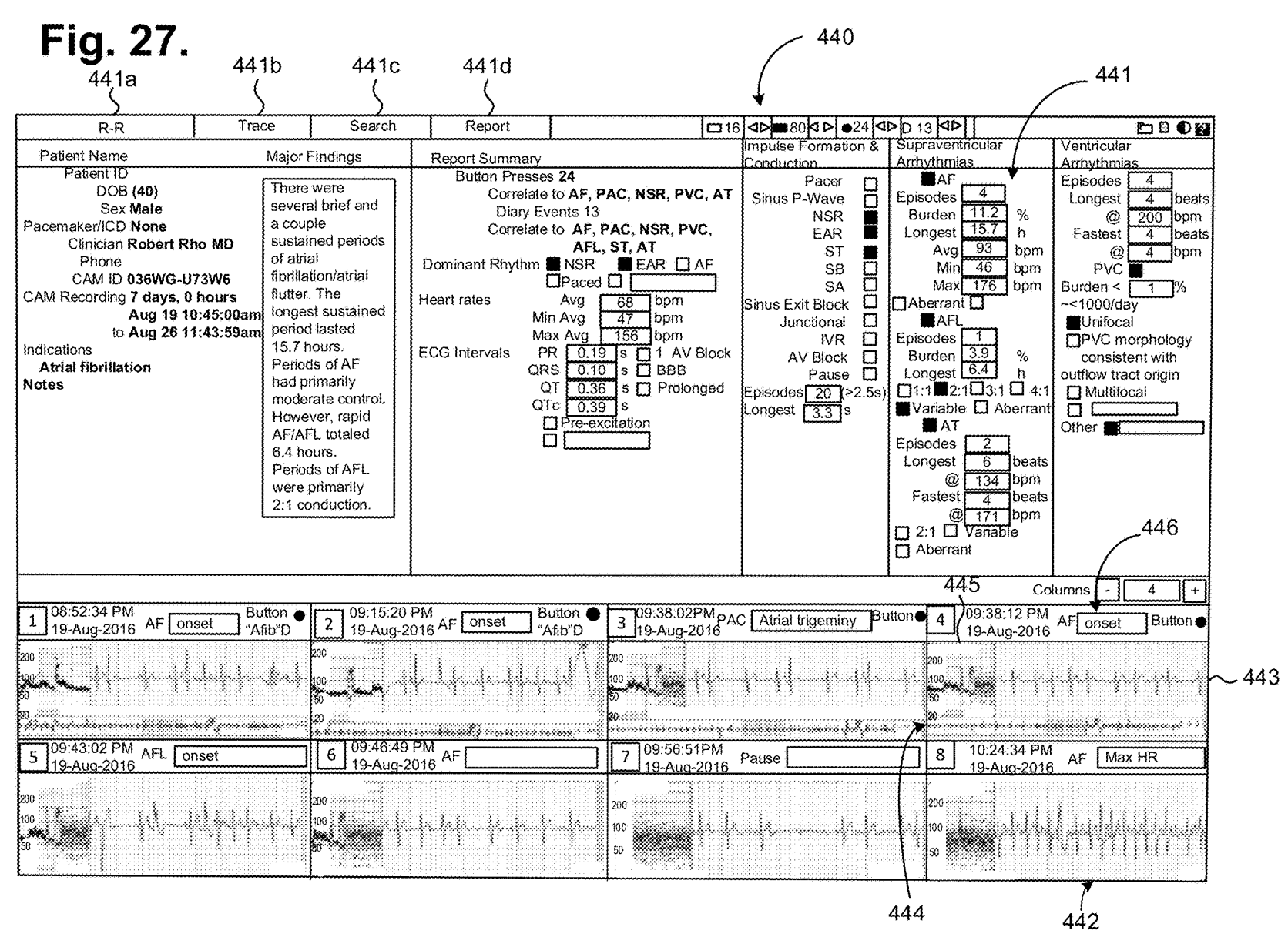

One or more of the runs or data strips can be identified and selected for use in a report for the patient. The report can be used by a medical professional to diagnose a cardiac condition of the patient. FIG. 27 is a diagram of an interactive user interface 440 for displaying data for inclusion in a patient report. The interactive interface can be implemented via a web page 240, which can include tabs 441a-d for an overview R-R plot web page 441a, trace plot 441b, search 441c, and report 441d. The web page 440 associated with the report tab 441d can include a rhythm summary bar 447 for the patient and one or more report strips 442 for including in a patient report to be provided to a physician or other medical professional for use in diagnosis of a patient. Each report strip 442 can include a diagnostic composite plot as described above in detail with respect to FIG. 6 based on a manually generated run or the automatically generated data strip as the far field view 444 with corresponding R-R interval data plots 445 and near-field views 446. The displayed report strips can include only a select set of report strips, such as those associated with runs or data strips exhibiting a particular cardiac rhythm or all the report strips generated for the patient based on the cardiac data obtained from the wearable ambulatory ECG monitor for that patient. For example, only those runs or data strips that are of particular significance can be selected for providing to a user, while the other runs or data strips can be brought to the medical professional's attention as a group, for instance as a number of each rhythm occurrence.

The rhythm summary bar 441 can include patient identification information and a checklist of cardiac rhythm patterns, which can be organized by category of pattern type and can include the same or different rhythm categories as the rhythm categories in the checklist of the overview 441a and trace 441b tabs. Additionally, the rhythm summary information is determined based on the report strips 442 selected for inclusion in the patient report.

Figure 28:
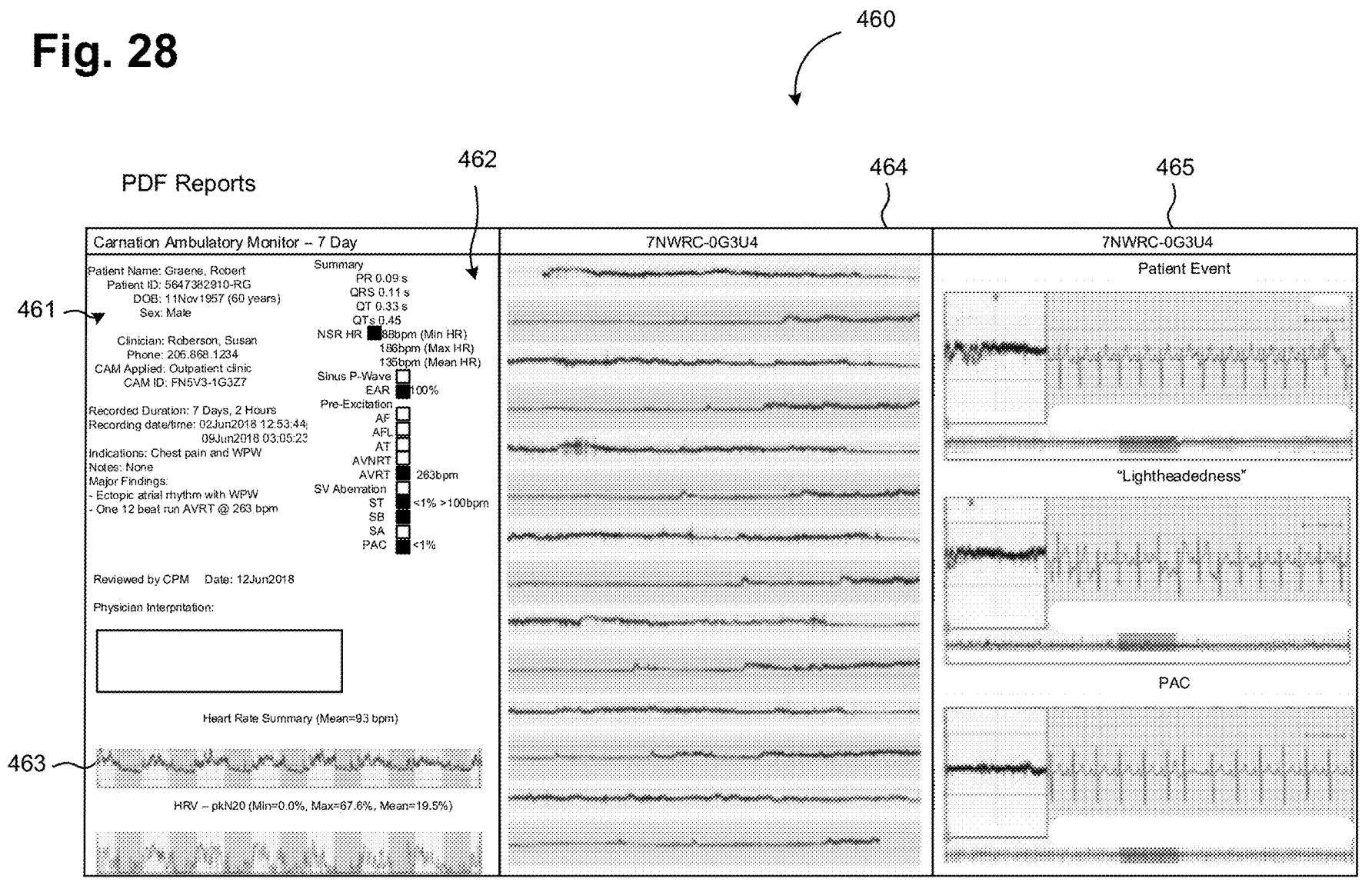

The report strips, along with the patient summary information, can be exported to generate a formal report provided to a medical professional for diagnosis and for inclusion in the patient's medical file. FIG. 28 is a view of a patient report 460. The patient report 460 can include patient identification information 461, a checklist of rhythm types 462, a heart rate summary 263, an overview R-R plot 464, and record strips 465. The patient identification information 461, such as name, identification number, date of birth, sex, type of cardiac monitor, physician, physician contact information, monitor application location, monitor identification number, monitor recordation duration, and monitor recording start and end dates. Other types of information are possible.

A checklist of rhythm types 462 can also be included in the report 460. The rhythm types can be the same or different than the rhythm types associated with the web pages for the overview and trace tabs R-R plot and ECG trace. Each of the rhythm types can be colored or highlighted based on a presence of that rhythm type in the cardiac data obtained from the wearable ambulatory ECG monitor. For example, rhythm types with black font indicate a presence of those rhythms in the cardiac data and the rhythms in gray font indicate that those rhythm types are not present in the cardiac data. Highlighting the rhythm types present in the cardiac data, while deemphasizing non-present rhythm types provides a quick view for the medical professional regarding cardiac events experienced by the patient. The checklist 462 can remain consistent across all patient reports, which allows the major findings of the cardiac data to include only the most important major findings since the checklist of rhythm types and heart rate summary give comprehensive results and allows each physician to focus on the area of the report believed to be most interesting.

The heart rate summary 463 can provide an average heart rate, as well as additional information, including a portion of an ECG trace. The overview R-R plot 464 can include R-R data points from cardiac data obtained over the recordation period of the ambulatory ECG monitor. Many rhythms often present in repeatable patterns and the overview R-R plot provides an overview of the frequency, duration, and time of day of various rhythms over the recording duration. The plot can be annotated with patient button presses, diary entries, and report strips, as described above. The annotations for the report strips can each act as a link to the corresponding report strip.

Figure 30:
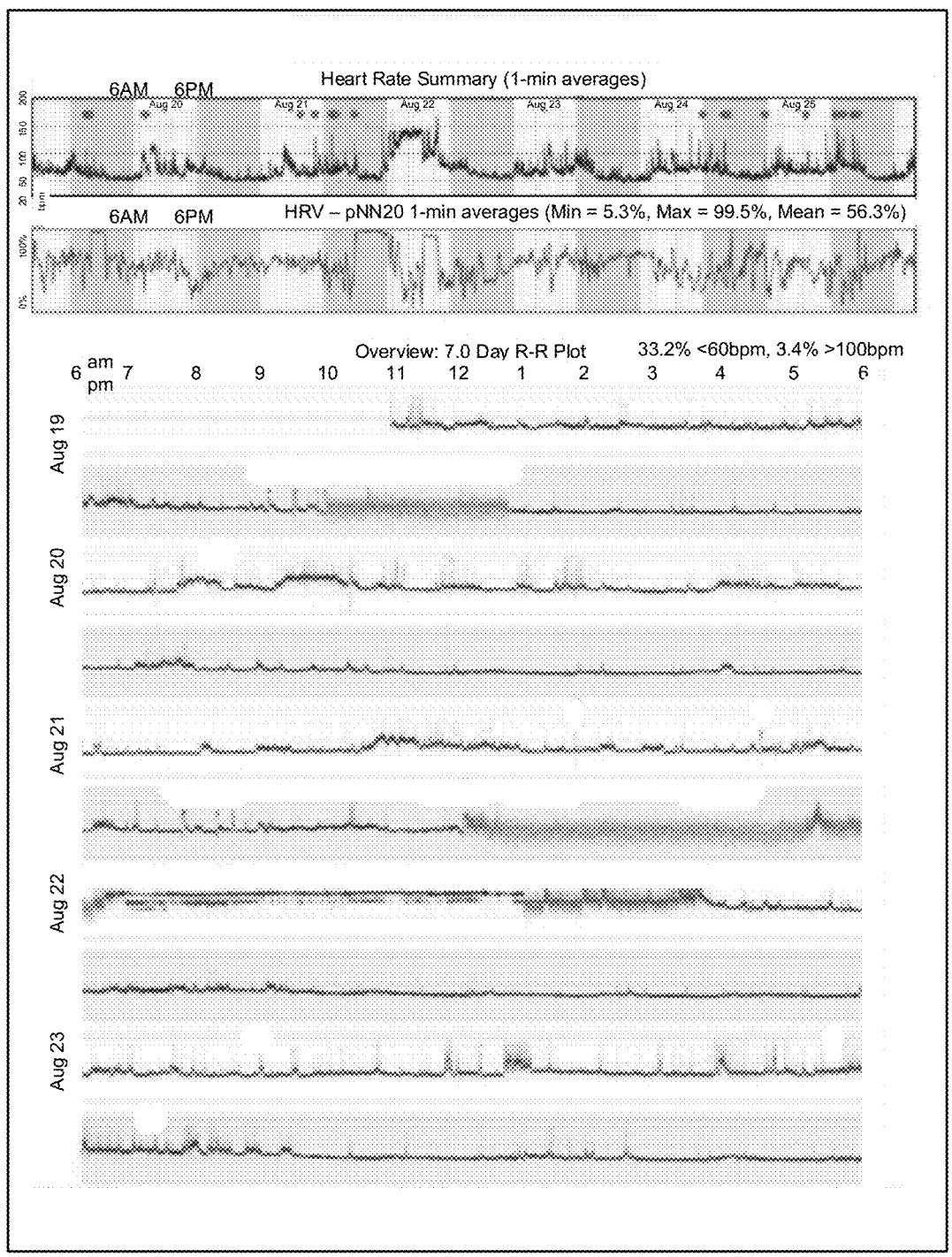
Figure 31:
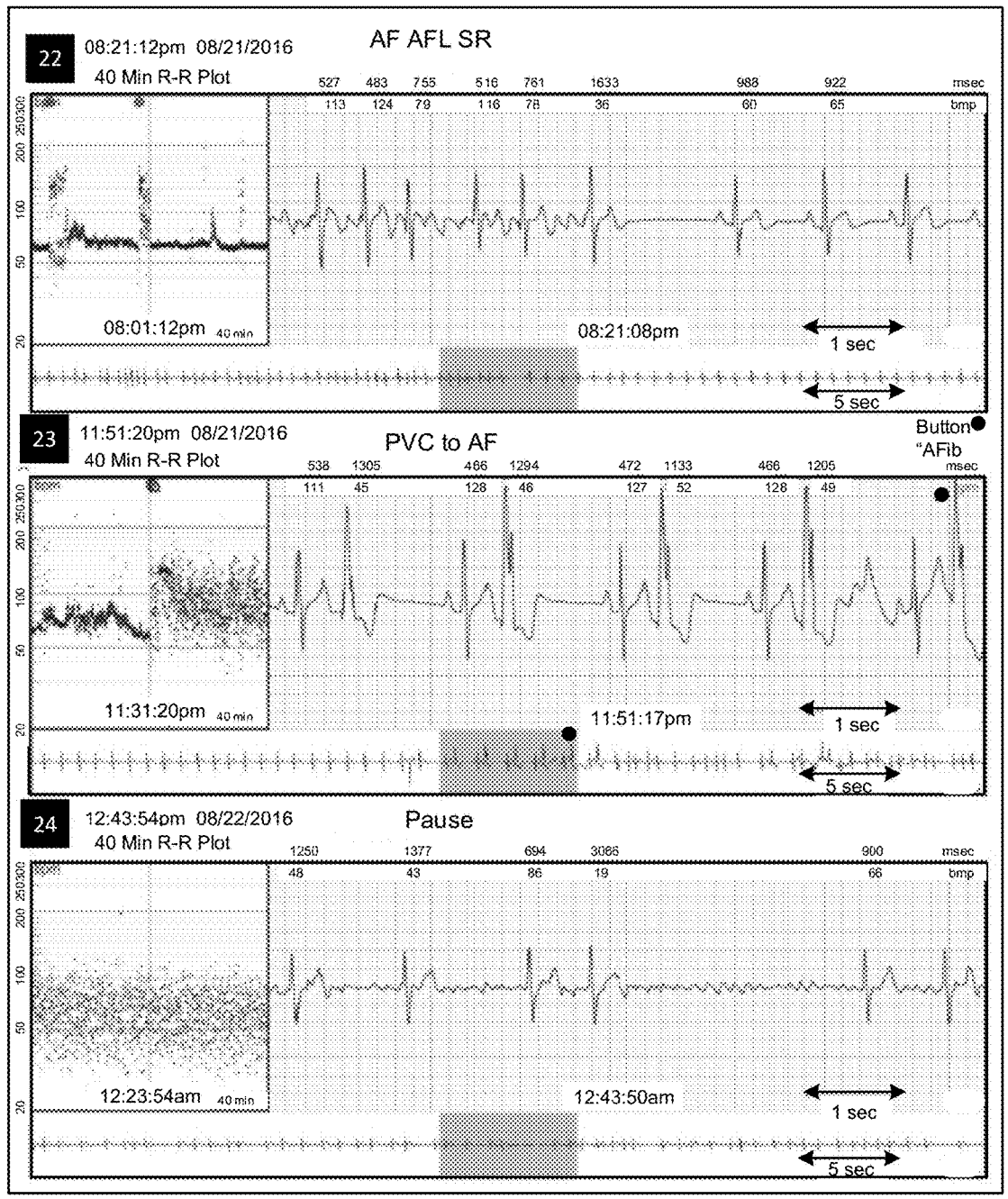

The report strips 465 generated for a patient from cardiac data recorded by the ambulatory ECG monitor can also be included in the report. Each report strip 465 can be annotated with an event or rhythm type. For example, if the patient has a diary entry for "lightheadedness," the data recorded during the time the patient experienced lightheadedness can be labeled "lightheadedness." Additionally, a portion of the cardiac data that resembles premature atrial contractions can be labeled PAC. FIGS. 29-31 are diagrams showing, the report of FIG. 28 in further detail.

Once generated, the report can be forwarded to a medical professional for review, analysis, and diagnosis of the patient's condition. Additionally, the report can be stored in a patient's electronic or paper medical file for later reference.

Interactions with the cardiac data are described above with respect to a mouse and a cursor; however, a user can also interact with the data using voice commands or multi-touch gestures on touch-enabled displays, which can greatly improve the communication interface between humans and machines. For example, in a log segment of information, a user wants to mark premature ventricular contraction events, which can occur by holding one finger on a PVC paint bucket provided in an interface and touching each PVC event in a waveform or ECG trace display. Other types of events can be marked the same way. Other touch gestures can include pinching portions of the interface to zoom in and out with time, two finger scrolling for changing an amplitude of a signal displayed, and one finger scrolling for moving a waveform up and down, and left and right. Double taps could bring up contextual menus, while tapping an onset or offset of a rhythm of interest with the right hand, while placing the left hand on a menu item of interest, or vice versa, allows a user to classify report strips or process portions of the R-R plot or ECG trace. Calipers, such as accessed via the paint box, can be used for basic interval measurements following size and rate expansion for quick PR, QRS, and QT measurements. Also, verbal commands can be added to hand commands for ease of use. Other types of gestures are possible.

In a further embodiment, physiological data collected via physiological sensors within or associated with the cardiac device can be displayed with the cardiac data. Further, sections of the physiological data can be selected based on abnormal results, rhythms, or measurements to create and store strips or runs. Such physiological sensors can collect physiological data, including heart rate, temperature, blood pressure, respiratory rate, blood pressure, blood sugar, oxygen saturation, minute ventilation, and so on; as well as physical states, such as movement, sleep, footsteps, and the like; and performance, including calories burned or estimated blood glucose level. Other types of physiological data are possible. When an abnormal measurement or data is identified from the physiological data, a time when that data was collected can be identified on the R-R plot or the ECG trace. For example, the oxygen rate of a patient can be identified as low and a time when the oxygen measurement was obtained can be determined. An indicator of the oxygen measurement can be placed within the R-R plot or ECG trace at the corresponding time to allow a medical professional to view the cardiac data that occurred when the patient's oxygen level was low. Further, data regarding body position and posture can be obtained for use with the cardiac data. For example, a position of a patient can be determined continuously, when a change in position is detected, periodically, or randomly. The positions can include supine, prone, upright, standing, and kneeling, as well as other types of positions. Use of the body position or posture can be helpful to identify unexpected changes in a patient's cardiac data. For instance, a patient is asleep during the night and a sudden increase in heart rate is identified. The increase could be due to a cardiac event, especially if the patient is still asleep and not performing any activity. Alternatively, if the patient's position is now upright, the increase could be due to the patient getting up and out of bed, and may be a normal heart rate for such activity.

The collected and displayed cardiac and physiological data can be obtained via a dermal cardiac device, such as described in detail in commonly-owned U.S. Pat. No. 9,433,367, issued Sep. 6, 2016, and in commonly-owned U.S. Pat. No. 10,433,748, issued Oct. 8, 2019, or via an implantable cardiac device, as described in further detail in commonly-owned U.S. Patent application Publication No. 2019/0167139, published Jun. 6, 2019, which are hereby incorporated by reference in their entirety.

While the invention has been particularly shown and described as referenced to the embodiments thereof, those skilled in the art will understand that the foregoing and other changes in form and detail may be made therein without departing from the spirit and scope.

What is claimed is:

1. A system for facilitating a cardiac rhythm disorder diagnosis with the aid of a digital computer, comprising:
   an electrocardiogram (ECG) monitoring and recording device worn by a patient and configured to record cutaneous action potentials of the patient;
   a download station adapted to retrieve the cutaneous action potentials recorded over a set period of time by the ECG monitoring and recording device as ECG data; and
   a processor and memory within which code for execution by the processor is stored, wherein the processor is configured to:
   generate a plot of R-R interval data based on the ECG data;
   provide a display of the R-R interval data comprising multiple rows of the R-R interval data; and
   change a presentation of the R-R interval data in the display by zooming in to a section of the R-R interval data in the presentation, comprising:
   identify the section of the R-R interval data in the display;
   remove a portion of the R-R interval data associated with an earlier recordation time than the R-R interval data in the section and located in at least a first of the rows;
   remove a portion of the R-R interval data associated with a later recordation time than the R-R interval data in the section and located in at least a last of the rows; and
   provide the R-R interval data remaining in the display in greater detail by spreading the remaining R-R interval data in display space previously occupied by the removed portion of the R-R interval data in the at least first row and the removed portion of the R-R interval data in the at least last row;
generate one or more report strips each comprising a segment of the remaining R-R interval data; and
classify each report strip with a cardiac condition of the patient.

2. A system according to claim 1, wherein each report strip is determined automatically or manually by a reviewer.

3. A system according to claim 1, wherein the processor is configured to zoom out of the presentation of the R-R interval data by providing the removed portions of R-R interval data.

4. A system according to claim 1, wherein the greater detail is provided, comprising:
stretching the remaining R-R interval data into parts of the display previously occupied by the removed portions of the R-R interval data.

5. A system according to claim 1, wherein the R-R interval data is arranged linearly in the rows in the display.

6. A system according to claim 5, wherein the rows are each numbered consecutively.

7. A system according to claim 6, wherein the row with the lowest number comprises the R-R interval data with an earliest recordation time and the row with the highest number comprises the R-R interval data with a latest recordation time.

8. A system according to claim 1, wherein the processor is configured to display at least one marker within the display.

9. A system according to claim 1, wherein the marker comprises an indicator for one of a time of day, cardiac event start or stop, and a patient marker.

10. A system according to claim 1, wherein the processor is configured to collect the report strips as a patient report.

11. A system for facilitating a cardiac rhythm disorder diagnosis with the aid of a digital computer, comprising:
a download station adapted to retrieve cutaneous action potentials of a patient recorded over a set period of time by an ECG monitoring and recording device as ECG data; and
a processor and memory within which code for execution by the processor is stored, wherein the processor is configured to:
generate a plot of R-R interval data based on the ECG data;
provide a display of the R-R interval data comprising multiple rows of the R-R interval data; and
change a presentation of the R-R interval data in the display by zooming in to a section of the R-R interval data in the presentation, comprising:
identify the section of the R-R interval data in the display;
remove a portion of the R-R interval data associated with an earlier recordation time than the R-R interval data in the section and located in at least a first of the rows;
remove a portion of the R-R interval data associated with a later recordation time than the R-R interval data in the section and located in at least a last of the rows; and
provide the R-R interval data remaining in the display in greater detail by spreading the remaining R-R interval data in display space previously occupied by the removed portion of the R-R interval data in the at least first row and the removed portion of the R-R interval data in the at least last row;
generate one or more report strips each comprising a segment of the remaining R-R interval data; and
classify each report strip with a cardiac condition of the patient.

12. A system according to claim 11, wherein each report strip is determined automatically or manually by a reviewer.

13. A system according to claim 11, wherein the processor is configured to zoom out of the presentation of the R-R interval data by providing the removed portions of R-R interval data.

14. A system according to claim 11, wherein the greater detail is provided, comprising:
stretching the remaining R-R interval data into parts of the display previously occupied by the removed portions of the R-R interval data.

15. A system according to claim 11, wherein the R-R interval data is arranged linearly in the rows in the display.

16. A system according to claim 15, wherein the rows are each numbered consecutively.

17. A system according to claim 16, wherein the row with the lowest number comprises the R-R interval data with an earliest recordation time and the row with the highest number comprises the R-R interval data with a latest recordation time.

18. A system according to claim 11, wherein the processor is configured to display at least one marker within the display.

19. A system according to claim 11, wherein the marker comprises an indicator for one of a time of day, cardiac event start or stop, and a patient marker.

20. A system according to claim 11, wherein the processor is configured to collect the report strips as a patient report.

* * * * *